United States Patent
Du et al.

(10) Patent No.: US 6,556,272 B1
(45) Date of Patent: Apr. 29, 2003

(54) MULTIMEDIA AND SCENT STORAGE MEDIUM AND PLAYBACK APPARATUS

(75) Inventors: Howard Du, New York, NY (US); Karl Alverson, Hoboken, NJ (US); Dah-Shiarim Chiao, New York, NY (US)

(73) Assignee: MultiSen Technology, Inc., New York, NY (US)

( * ) Notice: Subject to any disclaimer, the term of this patent is extended or adjusted under 35 U.S.C. 154(b) by 0 days.

(21) Appl. No.: 09/690,042

(22) Filed: Oct. 17, 2000

Related U.S. Application Data

(63) Continuation-in-part of application No. 09/593,219, filed on Jun. 14, 2000.

(51) Int. Cl.[7] .............................................. G03B 21/32
(52) U.S. Cl. ....................................................... 352/85
(58) Field of Search ........................................... 352/85

(56) References Cited

U.S. PATENT DOCUMENTS

| | | |
|---|---|---|
| 2,540,144 A | 2/1951 | Stern |
| 2,813,452 A | 11/1957 | Laube |
| 2,905,049 A | 9/1959 | Laube |
| 4,556,539 A | 12/1985 | Spector |
| 4,603,030 A | 7/1986 | McCarthy |
| 4,617,147 A | 10/1986 | Shinbani |
| 4,629,604 A | 12/1986 | Spector |
| 4,761,437 A | 8/1988 | Christie |
| 4,880,774 A | 11/1989 | Joukou et al. |
| 4,905,112 A | 2/1990 | Rhodes |
| D313,018 S | 12/1990 | Funabashi |
| 5,023,020 A | 6/1991 | Machida et al. |
| 5,071,621 A | 12/1991 | Tokuhiro et al. |
| 5,097,376 A | 3/1992 | Khan |
| 5,150,722 A | 9/1992 | Rutherford |
| 5,175,791 A | 12/1992 | Muderlak et al. |
| D338,204 S | 8/1993 | Takao |
| 5,314,669 A | 5/1994 | Hamilton |
| D349,496 S | 8/1994 | Sato |
| 5,398,070 A | 3/1995 | Lee |
| 5,429,180 A | 7/1995 | Nishino et al. |
| 5,460,787 A | 10/1995 | Colon |
| 5,480,591 A | 1/1996 | Lagneaux et al. |

(List continued on next page.)

FOREIGN PATENT DOCUMENTS

| | | |
|---|---|---|
| WO | WO 00/15268 | 3/2000 |
| WO | WO 00/15269 | 3/2000 |

*Primary Examiner*—Russell Adams
*Assistant Examiner*—Michelle Nguyen
(74) *Attorney, Agent, or Firm*—David M. O'Neill

(57) ABSTRACT

The multimedia and scent storage medium described herein comprises a multimedia storage region for storing multimedia information; a scent storage region for storing multiple scents; scent identification information for identifying which scents are stored in the scent storage region; and scent recovery information stored in the multimedia storage region for sequencing recovery of scents stored in the scent storage region to coincide with audio and/or video information stored in the multimedia region. The integrated system described herein comprises a multimedia and scent storage medium and a multimedia player and scent recovery system for use in conjunction with the multimedia and scent-bearing medium. The multimedia and scent recovery system comprises a multimedia playback system for recovering the multimedia information stored in the multimedia storage regions of the multimedia and scent storage medium; a scent recovery system for recovering scents stored in the scent storage region of the multimedia and scent storage medium; and user input and control means for permitting the user of the integrated system to input commands for controlling the playback of multimedia information and recovery of scents stored in the multimedia and scent-bearing medium.

47 Claims, 26 Drawing Sheets

U.S. PATENT DOCUMENTS

| | | | |
|---|---|---|---|
| 5,484,472 A | 1/1996 | Weinberg | |
| 5,503,332 A | 4/1996 | Glenn | |
| 5,565,148 A | 10/1996 | Pendergrass, Jr. | |
| 5,577,156 A | 11/1996 | Costello | |
| 5,590,769 A | 1/1997 | Lin | |
| 5,591,409 A | 1/1997 | Watkins | |
| 5,716,431 A | 2/1998 | von Glehn | |
| 5,724,256 A | 3/1998 | Lee et al. | |
| 5,734,590 A | 3/1998 | Tebbe | |
| 5,742,256 A | 4/1998 | Wakabayashi | |
| 5,805,768 A | 9/1998 | Schwartz et al. | |
| 5,813,614 A | 9/1998 | Coffee | |
| D399,202 S | 10/1998 | Kanatani | |
| 5,848,727 A | 12/1998 | Leo et al. | |
| D405,082 S | 2/1999 | Shibata | |
| 5,887,118 A * | 3/1999 | Huffman et al. | 392/390 |
| D408,408 S | 4/1999 | Ito et al. | |
| 5,939,033 A | 8/1999 | Kendall et al. | |
| D413,887 S | 9/1999 | Renk | |
| 5,949,522 A | 9/1999 | Manne | |
| 5,963,302 A | 10/1999 | Wittek | |
| 5,972,290 A | 10/1999 | De Sousa | |
| D416,897 S | 11/1999 | Ishii et al. | |
| 6,004,516 A | 12/1999 | Rasouli et al. | |
| 6,004,666 A | 12/1999 | Horning et al. | |
| 6,024,783 A | 2/2000 | Budman | |
| 6,025,902 A | 2/2000 | Wittek | |
| 6,041,023 A | 3/2000 | Lakhansingh | |
| 6,044,200 A | 3/2000 | Hirdes | |
| 6,044,202 A | 3/2000 | Junkel | |
| 6,053,738 A | 4/2000 | Ivey, Jr. | |
| 6,069,851 A | 5/2000 | Fenner | |
| D427,988 S | 7/2000 | Haney | |
| D430,444 S | 9/2000 | Allsop et al. | |
| D431,543 S | 10/2000 | Yuyama | |
| 6,282,458 B1 | 8/2001 | Murayama et al. | |
| 6,338,818 B2 | 1/2002 | Budman | |

\* cited by examiner

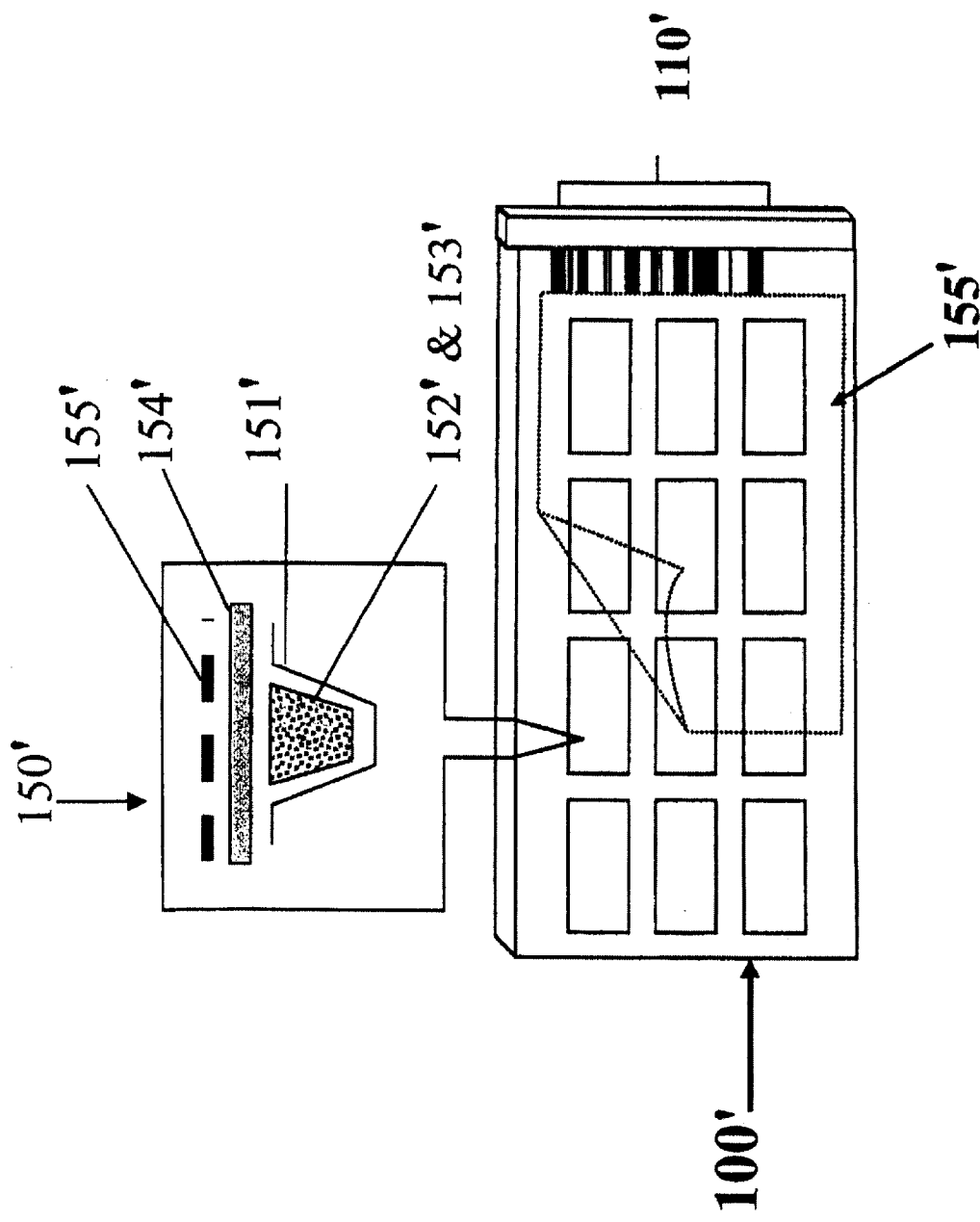

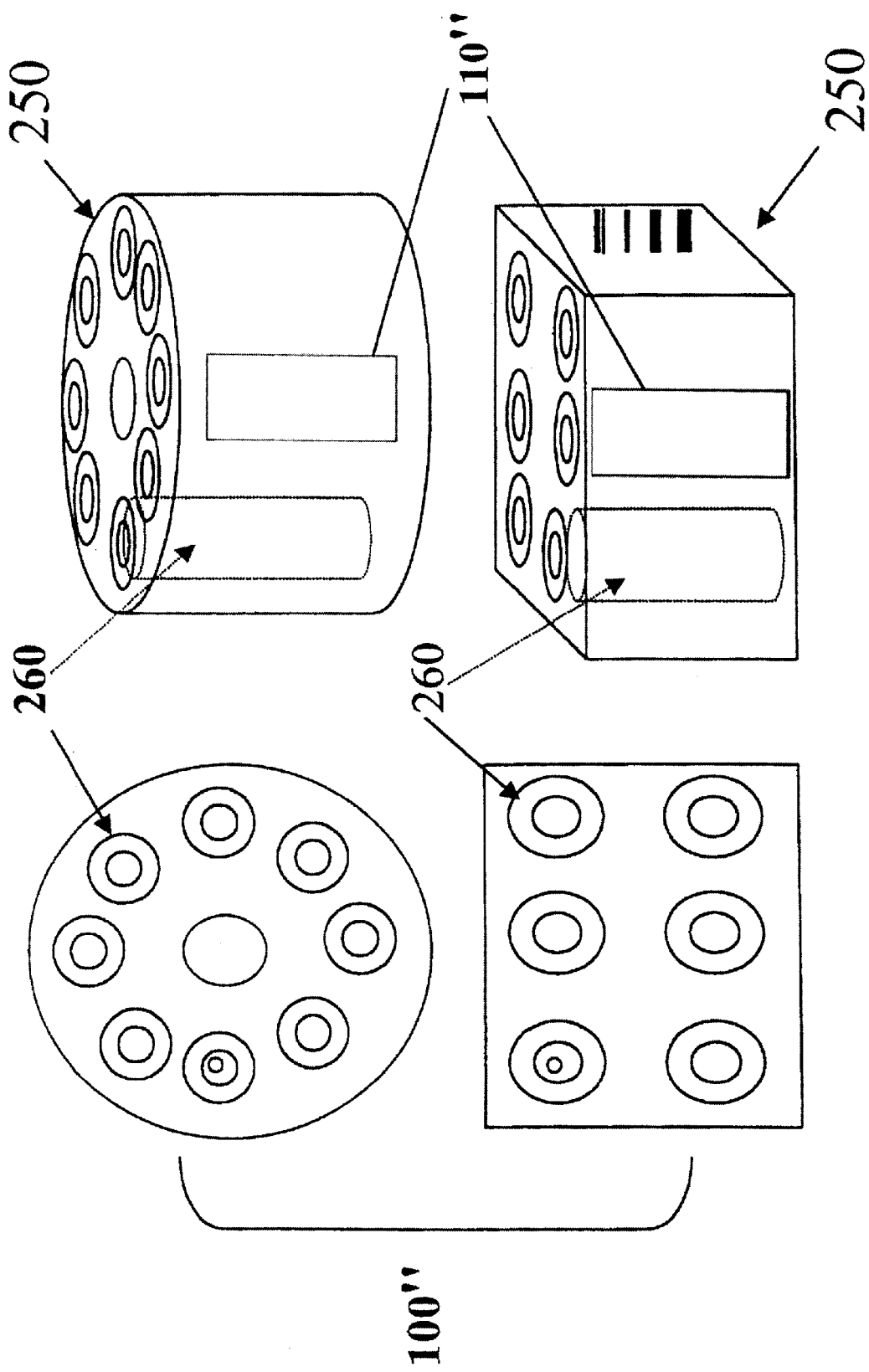

MULTIMEDIA AND SCENT STORAGE MEDIUM AND PLAYBACK APPARATUS

CROSS REFERENCE TO RELATED APPLICATION

This application is a continuation-in-part of a prior U.S. application with Ser. No. 09/593,219, filed Jun. 14, 2000 and entitled "MULTIMEDIA AND SCENT STORAGE MEDIUM AND PLAYBACK APPARATUS," which is hereby incorporated by reference in its entirety.

FIELD OF THE INVENTION

The invention relates to multimedia systems having scent-dispersing capability, and more particularly to a multimedia and scent storage medium for use in conjunction with an integrated multimedia playback and scent recovery system.

BACKGROUND OF THE INVENTION

Multimedia sources heretofore usually have been limited to audio or visual media. For example, the public is widely familiar with television, high fidelity audio, FM radio, and more recently, the Internet (which typically is audio-visual in format). As a result, the public has been limited to audio or visual stimulation. There has not been widespread media available for providing an olfactory ("scent") stimulation, particularly scent media that are intended to operate in synchronism with audio or visual sources. Thus users are prevented from experiencing a complete multi-sensory experience that would provide an authentic virtual reality experience.

Known prior art is deficient for many reasons. For example, the prior art shows little or no appreciation for the need to identify scent sources stored on media so that multiple scents stored in them may be recovered in a pre-programmed sequence. Other prior art is designed for use in large auditoriums or movie theaters and comprise multiple, separate and expensive components that are impractical for personal or home use. The prior art also shows no appreciation of the desirability to provide user-specifiable scent sequences for use in combination with audio or visual multimedia sources.

More specifically, U.S. Pat. No. 5,887,118 to Huffmnan et al. teaches an olfactory card including a scent producing member. Although the olfactory card of Huffman can be used for personal applications, it suffers from several limitations that prevent it from being of widespread use. The most noticeable limitation is that it is intended for use with PCMCIA slots in portable computers. PCMCIA cards are noticeably small and provide little room for storing the volume of scents that would be required for use in home multimedia applications. Further, in order to properly operate with the PCMCIA interface, the olfactory card requires a separate interface and on-board processing hardware and, as a result, represents an expensive and complex solution.

In addition, the PCMCIA card of U.S. Pat. No. 5,887,118 includes both the scent and the scent recovery apparatus in a single housing. Since the scent-recovery scent apparatus and associated electronics are relatively expensive, a user is presented with a dilemma. After the scent has been exhausted, the user either has to dispose of the PCMCIA card and purchase a new one with fresh scent, or send the PCMCIA card to a commercial entity for refilling. Either of these are less acceptable than an inexpensive disposable alternative. Further, Huffman et al. does not teach any means for editing pre-programmed scent recovery sequences so that a user may "customize" scent recovery sequences for use with known multimedia sources.

U.S. Pat. No. 6,004,516 to Rasouli et al. discloses a scent-bearing disk and associated playback apparatus. The system disclosed in U.S. Pat. No. 6,004,516 shows no appreciation of scent recovery and sequencing problems. For instance, there is no teaching of how separate scents on the disk are tagged so that they can be rapidly and accurately accessed during playback of multimedia content so that the scent recovery sequence coincides with the multimedia content.

U.S. Pat. No. 4,629,604 describes a player for a multi-aroma cartridge with individual electric heaters. The player disclosed therein provides no scent identification information for various replacement cartridges, nor is it an Internet-compatible device. Not having any tag or scent identification information limits the flexibility of the player disclosed in U.S. Pat. No. 4,629,604.

U.S. Pat. No. 5,949,522 describes a device that can deliver various combinations of scent in rapid succession to a user's nose in conjunction with videographic images or sounds. Through proper control of valves and compressed air, the system described in U.S. Pat. No. 5,949,522 can use liquid fragrance without heating. U.S. Pat. No. 5,949,522 shows no appreciation of the need for tag or fragrance identification information to control the sequential recovery of fragrances from the fragrance containers. This limits the modes of operation and in turn the flexibility of the system. Furthermore, the whole system requires an uncomfortable and unsanitary nose tube.

U.S. Pat. No. 5,591,409 describes a method and apparatus for "metered spray" aroma delivery system for use with an entertainment system. The method and apparatus disclosed in U.S. Pat. No. 5,591,409 uses liquid fragrance without heating, and a limited number of fragrance containers without tag or scent identification information. This again limits the flexibility of operation of the device.

U.S. Pat. No. 6,053,738 describes an apparatus for reproducing smells and flavors using a cylindrical housing containing smell and flavor cartridges. U.S. Pat. No. 6,053,738 provides no tag information for future smell and taste replacements.

U.S. Pat. No. 5,565,148 describes a multiple aroma delivery apparatus with a plurality of separate cylindrically-shaped chambers. Limiting the arrangement of chambers and valves also decreases the variety of scents deliverable by the system.

U.S. Pat. No. 5,734,590 describes a device comprising a plurality of stimulus generators including a scent generator, with a micro-encapsulated scent carrier or a block of spray tubes. The utility signal source is from a separate recording medium. The system disclosed in U.S. Pat. No. 5,734,590 provides no tag or scent identification information for the scent carrier and lacks the ability to be re-programmed.

U.S. Pat. No. 6,025,902 describes a process for increasing the sensual perception of visual, acoustic, and odor stimulation in a theatre. U.S. Pat. No. 5,963,302 also describes a process for increasing the sensual perception of visual, acoustic, and scent stimulation in a theatre, as well as various scent storing and releasing arrangements.

U.S. Pat. No. 6,024,783 describes a multimedia-linked apparatus for delivery of real-time or stored aroma. The aroma-producing system is a multi-chamber mechanism. The aroma emitting material is individually placed above each heater in each releasing chamber, and each chamber has it own air exhausting unit and a controlled opening door.

However, the system disclosed in U.S. Pat. No. 6,024,783 is based on scent or aroma carriers (i.e., card, disk, cartridge, container, or cylinder) that do not carry any tag or scent identification information within or on the scent or aroma carriers. Without any tag or scent identification information, the control device of the prior art cannot receive the tag information of scents or aroma. Thus the scents cannot be recovered in a preprogrammed sequence.

Providing tag or scent identification information for the scent or aroma carriers with a controller would generate more variety and precision with respect to scent or aroma recovery in a very cost-efficient way. In addition, the multimedia information recovered from the multimedia medium of the scent or aroma carriers would create another option for users, as a stand-alone multimedia playback and scent recovery device. The prior art shows no appreciation of these modes of operation.

There are different methods and apparatus for impregnating scent medium on a disk or a card to make a Scent Disk or a Scent Card or a Scent Cartridge. For example, U.S. Pat. No. 5,939,033 describes a method and apparatus for impregnating solid materials (e.g. hydrogen peroxide) on a disk allowing conductive foil to conduct heat. U.S. Pat. No. 5,972,290 describes a process and apparatus for programmed scent delivery by piercing capsules of scented substrates and compounds embedded on a disk. U.S. Pat. No. 5,848,727 discloses a strip dispenser that is manually generated. U.S. Pat. No. 5,460,787 presents a method and apparatus for an insertable scented card. U.S. Pat. No. 6,044,202 describes an apparatus and method for a heated deodorizing scent card with a body of fragrance compound and an embedded plurality of individual and heat generating resistors operated via a thermistor.

There are also different methods and apparatus for improving scent cartridges. U.S. Pat. No. 5,314,669 describes a multi-layer cylindrical system to dispense different scents without changing the retaining carriage. U.S. Pat. No. 5,023,020 also describes a cylindrical receptor with plural containers for receiving scents. U.S. Pat. No. 5,742,256 describes a computer-controlled metered-delivery device, which dispenses scents onto a rotating absorptive porous member.

There are different methods and apparatus for applying gas permeable membrane materials to control scent release. U.S. Pat. No. 5,150,722 describes a method for effecting the controlled release of fragrance in a relatively "long period." U.S. Pat. No. 5,480,591 describes a "naturally" diffusing diffuser with membranes on the flank.

With respect to recording media with scent, U.S. Pat. No. 5,097,376 describes a container with a fragrance material, in particular, a tape cassette with embedded scent. However, the embedded fragrance only serves for identification purposes and shows no appreciation of the use of multiple scents. U.S. Pat. No. 6,004,666 discloses a data carrier having fracturable microencapsulated scents releasable upon fracturing the micro-capsules.

Timing controlled scent diffusion methods have been used to diffuse scents in air, with some attempts to develop aroma-delivering apparatuses with timing control. U.S. Pat. No. 4,603,030 describes a scent-emitting system to propel scents in response to a programmed sequence of scents of predetermined duration. U.S. Pat. No. 5,175,791 describes a stepped power control fragrance diffuser with fragrance-emitting blocks within certain pre-programmed time period. U.S. Pat. No. 5,805,768 describes an apparatus with a rotating plurality of receptacles for various scents, allowing the user to pre-select a variety of aroma to be delivered at predetermined time intervals.

There have been some attempts to develop a neutralizing method to increase the sensitivity and perception level between scent releasing. U.S. Pat. No. 5,429,180 describes a process and apparatus for introducing refreshing-type aromatic agent between relaxing-type aromatic agents in a repetition of cycles. This prior art does not provide neutralizing or masking function that synchronizes with multimedia presentation.

Thus, a multimedia and scent recovery system that is capable of storing multiple scents in sufficient quantity is desirable so that a user may use it in a home environment in combination with a multimedia playback means to create a realistic virtual reality experience that may include audio or visual stimulation in combination with scent stimulation. A relatively simple storage medium that combines both multimedia information and multiple scents that would also facilitate a realistic virtual reality experience that may be repeated over and over again is also desired. In addition, an editing means that permits a user to depart from a pre-programmed scent recovery sequence in order so that the user may create a "customized" virtual reality experience, including multimedia and scent elements is also desired.

SUMMARY OF THE INVENTION

The limitations of the prior art are overcome in the following embodiments of the present invention. A first embodiment of the present invention comprises a multimedia and scent storage medium, further comprising a multimedia storage region for storing multimedia information; a scent storage region for storing multiple scents; scent identification information for identifying which scents are stored in the scent storage region; and scent recovery information stored in the multimedia storage region for sequencing recovery of scents stored in the scent storage region to coincide with audio and/or video information stored in the multimedia region. The multimedia information stored in the multimedia region may comprise audio, video, textual, graphical or photographic information.

A variation of the first embodiment comprises a multimedia and scent-bearing medium having a plurality of recessed three-dimensional regions for storing separate scents; inert storage media deposited within the regions for storing separate scents; and a gas permeable membrane placed over upwardly-facing openings of the recessed three-dimensional regions. The gas permeable membrane may comprise a microporous or macroporous polymer.

Another variation of the first embodiment of the present invention comprises the multimedia and scent-bearing media of the foregoing embodiments in combination with scent recovery sequence information for controlling the sequential recovery of scents stored in the scent storage region.

In a further variation of the first embodiment of the present invention, the scent recovery sequence information of the preceding embodiments further facilitates the simultaneous recovery of scent and multimedia information to provide an immersive multi-sensory experience. In this further variation scent-neutralizing or scent-masking materials are also stored in the multimedia and scent-bearing medium. The scent-neutralizing or scent-masking material is used to mask the previous scents recovered from the multimedia and scent-bearing medium before additional scents are released.

In yet another variation of the first embodiment of the present invention, the multimedia and scent-bearing medium comprises a housing having multiple storage slots, a plurality of scents stored within each slot in canisters; and a scent identification means. Each canister has a release valve for facilitating the release of scents from the canister. The scent identification means identifies which scents are stored in which slots. Bar codes may be used as the scent identification means.

Further variations of the first embodiment of the present invention overcome the limitations of the prior art with respect to the storage of volatile scents. In one embodiment the multimedia and scent-bearing medium is stored in a storage case having overlapping seals to prevent scent from escaping from the scent storage region. In another embodiment a gas impermeable membrane is placed over the gas permeable membrane covering the recessed three-dimensional regions (each of which stores a separate scent) of the multimedia and scent-bearing medium to prevent scent from escaping from the recessed three-dimensional regions.

A second embodiment of the present invention comprises an integrated system having a multimedia and scent storage medium and a multimedia player and scent recovery system for use in conjunction with the multimedia and scent-bearing medium. The multimedia playback and scent recovery system of the second embodiment comprises a multimedia playback system for recovering the multimedia information stored in the multimedia storage regions of the multimedia and scent storage medium; a scent recovery system for recovering scents stored in the scent storage region of the multimedia and scent storage medium; and user input and control means for permitting the user of the integrated system to input commands for controlling the playback of multimedia information and recovery of scents stored in the multimedia and scent-bearing medium.

A variation of the second embodiment comprises a multimedia player having an optical (e.g. CD, DVD, or bar code) or magnetic playback system (e.g. floppy, hard disk, or tape) for retrieving the encoded multimedia information. The audio signal recovered from the multimedia information can be played back through a speaker system that is connected to an amplifier system. The video signal recovered from the multimedia information can be played back through a visual display system (e.g. a monitor or a LCD).

Another variation of the second embodiment of the present invention comprises an interactive playback system to edit the pre-programmed scent recovery sequence information retrieved from the multimedia and scent-bearing medium for controlling the sequential recovery of scents stored in the scent storage region. The editing function of the present invention allows a user to create a user-specified scent recovery sequence by editing the scent recovery sequence information recovered from the multimedia and scent-bearing medium. Using the editing function, a user may alter the order of scent recovery; change the duration of recovery of individual scents, or substitute other scents for those specified by the pre-programmed scent recovery sequence information. The editing means also permits a user to create entirely new scent recovery sequences to be used in conjunction with multimedia information.

In a further variation of the second embodiment of the present invention, the scent recovery system may comprise single or multiple, movable heating elements. The scent recovery system converts the scent recovery sequence information recovered from the multimedia and scent storage medium into control signals for controlling the operation of the heating elements. Upon receiving the control signal, the heating elements (e.g. laser or infrared) will move to a predetermined position so that they may heat and thereby release the heat-releasable scents stored within the scent-bearing medium. Through a ductwork immediately adjacent to the multimedia and scent-bearing medium, a fan will facilitate the venting of scents to the user of the integrated system.

Yet another variation of the second embodiment of the present invention comprises an input connection for accepting a multimedia signal from a remote source. The remote multimedia source may comprise radio, television, or satellite transmitters, or publicly switched telephone networks (PSTN) or cable systems, or LAN, or WAN, or a computer. The remote multimedia information may comprise separately-recoverable segments and may further comprise audio, video textual, graphical or photographic information.

Still further variations of the second embodiment of the present invention overcome the limitations of the prior art with respect to the variety of scents storage media. By retrieving the tagging, scent recovery sequence, and the multimedia information from the multimedia medium or remote source and storing all of this information in a local storage system, the present invention not only provides precise coupling between scents and scent recovery sequence information but also allows the user to edit or transmit specified scent recovery sequences and multimedia information to another user.

A third embodiment of the present invention comprises a multimedia playback and scent recovery system for use with a multimedia and scent-bearing medium in disc format. This variant has a semicircular housing having a bottom surface, a curved upper surface, and a vertical surface. The housing contains a multimedia playback means for recovering the multimedia information stored in the multimedia storage means and a scent recovery means for recovering the scents stored in the scent storage means. The vertical surface has a slot for accepting the multimedia and scent-bearing disc. The multimedia playback and scent recovery system has in its upper surface a plurality of vents for permitting scents released from the multimedia and scent storage disc by the scent recovery means to be dispersed into the atmosphere. In variations of the third preferred embodiment, various combinations of control buttons are positioned in the upper surface of the multimedia playback and scent recovery system. These buttons may be used for simple playback of pre-programmed multimedia and scent recovery sequences, or they may be used to program new multimedia and scent recovery sequences. In other variations, a liquid crystal display screen or other suitable display technology may be incorporated either to monitor the progress of playback, or to display the various pre-programmed multimedia and scent recovery sequences available for playback, or to assist in programming new or "custom" multimedia playback and scent recovery sequences. The multimedia playback and scent recovery system of the third preferred embodiment also has interfacing means for connecting the system to peripheral systems. For example, the interfacing means may be used to connect the multimedia playback and scent recovery system to a monitor and speaker system so that the multimedia information recovered from the multimedia and scent storage disc may be viewed in conjunction with scent release. Alternatively, the interfacing means may be used to connect the multimedia playback and scent recovery system to a remote computer so that more complex programming sequences may be implemented.

The multimedia playback and scent recovery system of the third preferred embodiment also comprises a retractable semicircular shield for protecting the multimedia and scent storage disc from damage while in use. During operation, the user would slide the retractable semicircular shield to remove or insert a multimedia and scent storage disk. In variations of the third preferred embodiment, the retractable shield may be motor-driven, in which case a user would control the position of the retractable shield either by using a push-button, or by a pressure-sensitive switch that upon sensing slight movement of the retractable shield would fully retract or close the shield. The retractable shield may be made from plastic or other suitable materials known to those skilled in the art. In various embodiments the shield may be transparent, translucent or opaque.

The third preferred embodiment can also be constructed in different physical configurations. For example, the housing may be rectangular and of sufficient size to fully enclose the multimedia and scent storage disc. In other configurations, the housing may have a circular, clam-shell configuration. Each of these configurations would serve the objective of providing a portable multimedia playback and scent recovery system.

Thus, it is seen that embodiments of the present invention overcome limitations of the prior art. Known scent storage media do not include information identifying either which scents are stored or what sequence the scents are to be recovered from the scent storage media. In contrast, the present invention stores scent identification and scent recovery sequence information in the multimedia and scent storage medium, thereby permitting the synchronized recovery of multimedia information and scents stored in the multimedia and scent storage medium. This manner of operation provides an immersive, multi-sensory experience.

Other known scent storage media require complex circuitry, processing capability, and heating elements for releasing scent from the scent storage media. Such media are complex in construction, expensive to manufacture, and expensive to purchase. In contrast, the multimedia and scent storage medium of the present invention is designed to operate with an integrated multimedia playback and scent recovery system that includes playback and scent recovery hardware. In consequence, the multimedia playback and scent recovery hardware need not be positioned on the multimedia and scent storage medium. As a result, the multimedia and scent storage medium of the present invention is simple in construction, inexpensive to manufacture, and inexpensive to purchase.

There are no known, integrated multimedia playback and scent recovery systems. As a result, it is difficult, if not impossible, to create synchronized multimedia playback and scent recovery sequences that are repeatable. Further, it is also difficult to develop new synchronized multimedia playback and scent recovery sequences. In contrast, the multimedia playback and scent recovery system of the present invention is designed to operate with multimedia and scent storage media that store scent identification and scent recovery sequence information. As a result, a user of the multimedia playback and scent recovery system can "replay" synchronized multimedia and scent recovery sequences to provide an immersive, multi-sensory experience that is repeatable. Further, the multimedia playback and scent recovery system of the present invention further comprises scent recovery sequence information storage means, and scent recovery sequence information editing means. In contrast to the prior art, this feature of the present invention permits a user to edit pre-programmed multimedia playback and scent recovery sequences to create new, "custom," user-specified multimedia playback and scent recovery sequences. Further, this feature of the present invention also permits a user to create entirely new multimedia playback and scent recovery sequences.

BRIEF DESCRIPTION OF THE FIGURES

The above and other objects and advantages of this invention will be apparent upon consideration of the following detailed description, taken in conjunction with the accompanying drawings in which like reference characters refer to like elements throughout, and in which:

FIG. 3 depicts a top view of an alternate multimedia and scent-bearing medium 100', and a cross-sectional view of a scent-bearing medium 150', made in accordance with a first preferred embodiment of the present invention;

FIG. 4 depicts multiple views of an alternate multimedia and scent-bearing medium 100" made in accordance with a first preferred embodiment of the present invention;

DETAILED DESCRIPTION OF THE PREFERRED EMBODIMENTS

The features and advantages of the present invention are illustrated in detail in the accompanying drawings, wherein like reference numbers refer to like elements throughout the drawings.

I. First Preferred Embodiment

Figure 1:
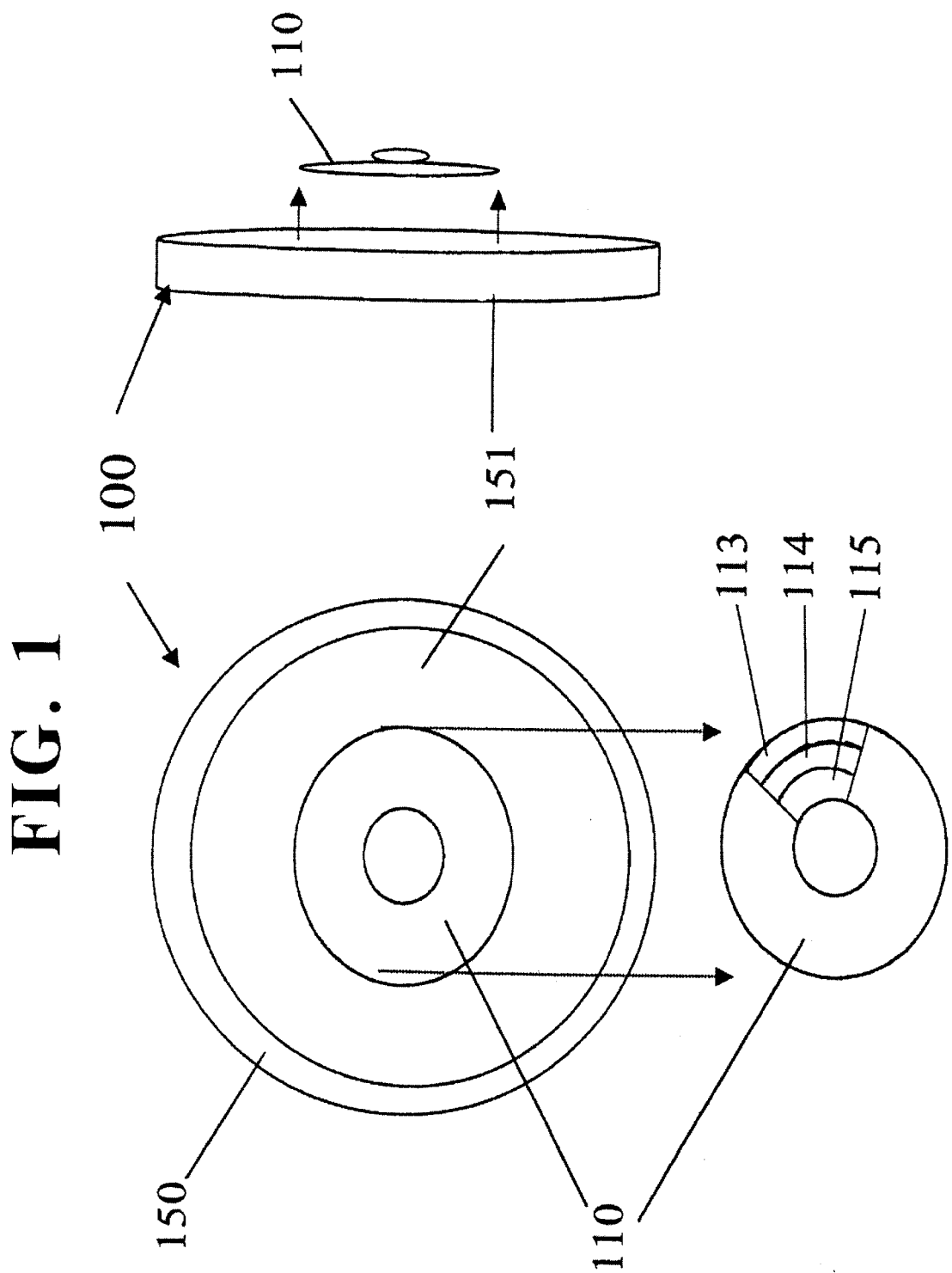
FIG. 1 depicts top and side views of a multimedia and scent-bearing medium 100 made in accordance with a first preferred embodiment of the present invention.
Figure 2A:
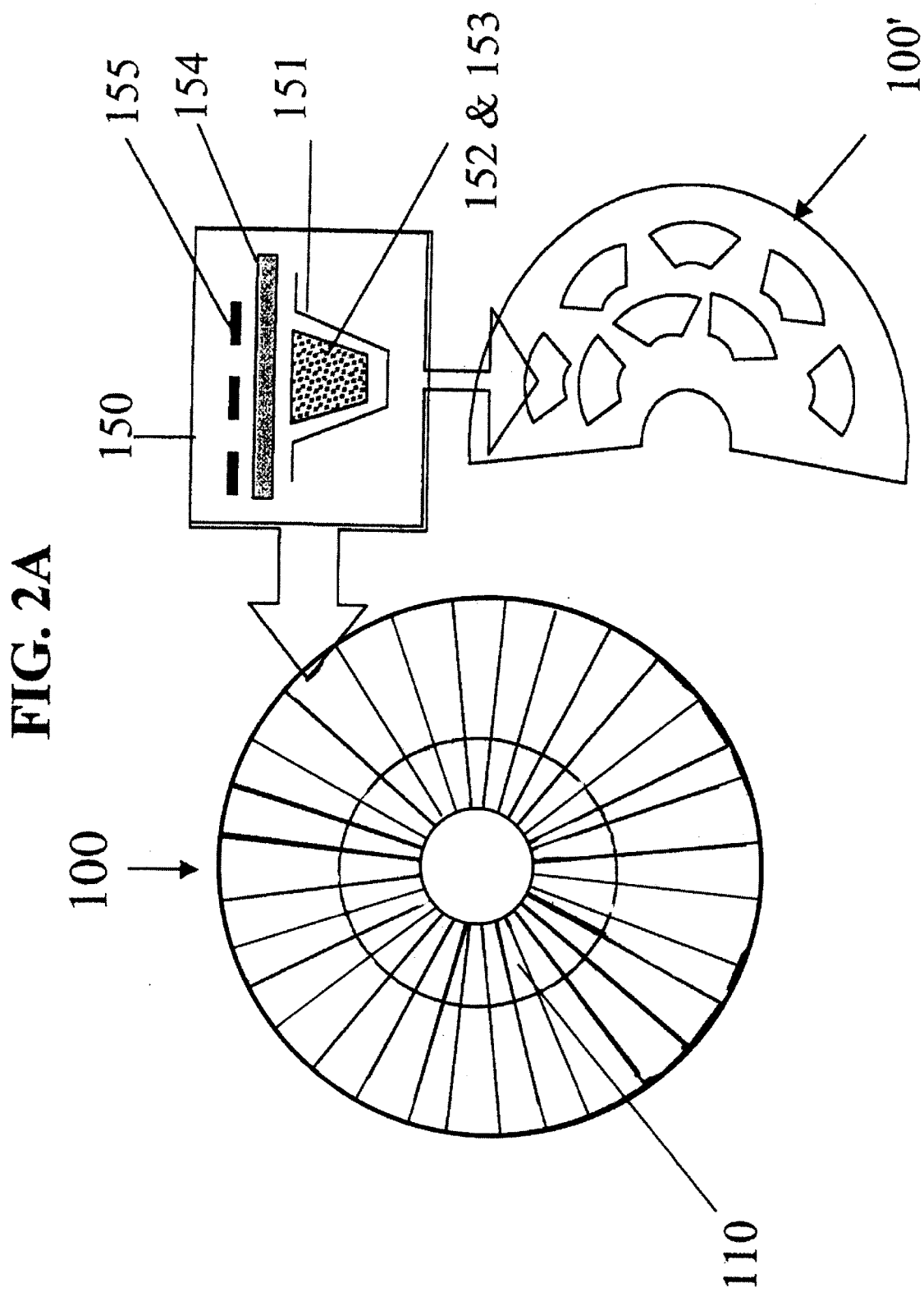
FIG. 2A depicts a top view of a multimedia and scent-bearing medium 100, and in particular a cross-sectional view of a scent-bearing medium 150, made in accordance with a first preferred embodiment of the present invention.

A first preferred embodiment of the present invention comprises a multimedia and scent-bearing medium 100 as depicted in FIGS. 1 and 2A. The multimedia and scent-bearing medium 100 comprises two elements: a multimedia storage medium 110 and a scent-bearing medium 150. The scent-bearing medium 150 further comprises a plurality of recessed three-dimensional regions 151 each for storing a separate scent.

Deposited within each three-dimensional region is an inert storage medium 152. The inert storage medium 152 is not reactive with the scents that will be stored within it. The three-dimensional region is formed in the plastic housing of the multimedia and scent-bearing medium 100. A plurality of radially-extending three-dimensional regions are shown in the multimedia and scent-bearing medium 100 depicted in FIG. 2A. The three-dimensional regions may also take concentric forms 151' as shown in the partial view of the multimedia and scent-bearing medium 100' also shown in FIG. 2A. The inert storage medium 152 may be a polymer gel and may take other forms that are well known to those of ordinary skill in the art.

A scent 153 is stored in the inert storage medium 152 shown in the cross-sectional view of FIG. 2A. The scent 153 is preferably heat releasable. In addition, a gas permeable membrane 154 is placed over each recessed three-dimensional region 151. The gas permeable membrane 154 permits scent 153 to escape from the recessed three-dimensional region 151 when heated.

A gas impermeable membrane 155 is shown in ghost view in the cross-sectional view of FIG. 2A. The gas impermeable membrane 155 is used for sealing purposes and is preferably reusable. The gas impermeable membrane 155 prevents the scents 153 stored in recessed three-dimensional region 151 in the multimedia and scent-bearing medium 100 from escaping when the multimedia and scent-bearing medium 100 is not in use.

The multimedia information is stored in the multimedia storage medium 110 of the multimedia and scent-bearing medium 100. The multimedia storage medium 110 in the embodiments depicted in FIGS. 1 and 2A corresponds to the conventional CD-ROM recording format. The multimedia information can also be stored in the multimedia region 110 using other formats, for example, DVD. Utilization of the DVD format will provide for greater storage capacity. The multimedia information stored in the multimedia storage medium 110 may take many forms including, for example, video, audio, textual, graphical, and photographic. As shown in the audio and video embodiment depicted in FIG. 1, audio information is digitally encoded using well known digital encoding formats in the region 113. Video information is also digitally encoded using well-known digital encoding formats in the region 114.

Digital scent identification information and scent recovery sequence information are stored in the scent region 115. The digital scent identification information identifies which scents are stored in which recessed three-dimensional regions 151. The scent recovery sequence information is used to synchronize scent recovery with the playback of multimedia information stored in the multimedia region 110. For example, the scent recovery sequence information could be used to recover a gun powder scent to coincide with the canon shot recorded in an audio recording of Tchaikovsky's 1812 Overture. In another embodiment, the scent recovery sequence information could be used to recover flower scents stored in the scent storage region 151 recovered from scent storage medium 150.

The multimedia information encoded in the multimedia storage medium 110 preferably may be segregated into separately recoverable segments. This would be particularly useful for use with interactive playback systems (e.g., an interactive multimedia game). Particular scents or particular sequence of scents would be programmed to coincide with particular multimedia segments to give an immersive multi-sensory experience.

Figure 2B:
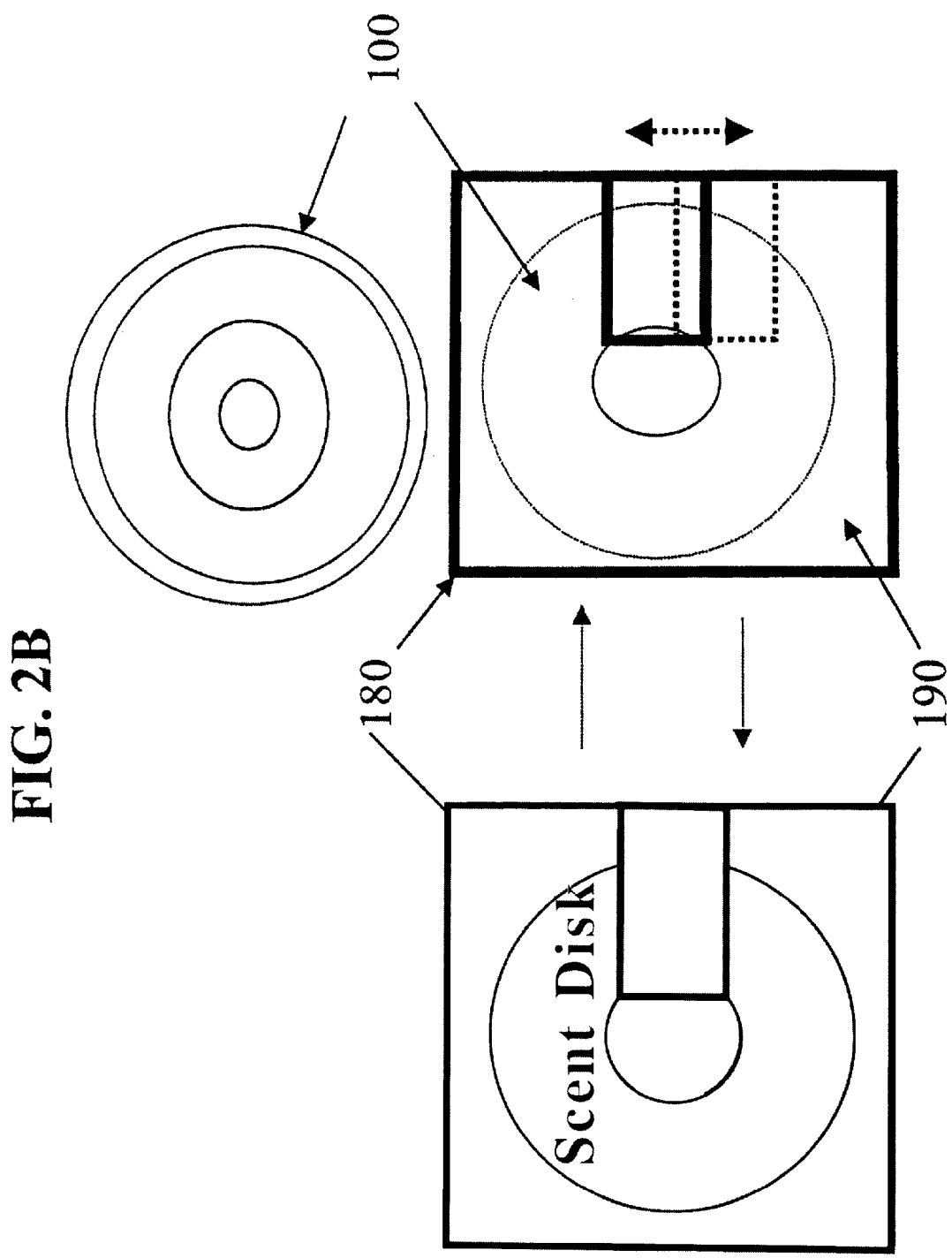
FIG. 2B depicts a multimedia and scent storage medium 100 placed in storage case 180, and made in accordance with a first preferred embodiment of the present invention.

Preferably a storage case 180 having overlapping seals 190 is used to store the multimedia and scent-bearing medium 100 depicted in FIG. 2B. The overlapping seals 190 prevent scents from escaping from the multimedia and scent-bearing medium 100.

In a variant of the first preferred embodiment shown in FIG. 3, the multimedia and scent-bearing medium 100' uses a magnetic memory in place of the optical storage medium depicted in FIGS. 1 and 2A. Information is recovered from magnetic memory electrically. As in the case of the first preferred embodiment, scent is stored in scent-bearing medium 150' in a plurality of recessed three-dimensional regions 151'. In this particular variant the regions take a rectangular form. The recessed three-dimensional regions 151' are also shown in cross-section in FIG. 3. Also as in the case of the first preferred embodiment, scent 153' is stored in an inert storage medium 152'. The scent 153' is preferably heat releasable. In addition, a gas permeable membrane 154' is placed over each recessed three-dimensional region 151'. The gas permeable membrane 154' permits scent 153' to escape from the recessed three-dimensional region 151' when heated. A gas impermeable membrane 155' is shown in ghost view in the cross-sectional view of FIG. 3. The gas impermeable membrane 155' is used for sealing purposes and is preferably reusable. The gas impermeable membrane 155' prevents the scents 153' stored in recessed three-dimensional region 151' in the multimedia and scent-bearing medium 100' from escaping when the multimedia and scent-bearing medium 100' is not in use.

In another variant of the first preferred embodiment depicted in FIG. 4, multimedia and scent storage medium 100" stores scent in a plurality of scent canisters 260. The scent canisters 260 are stored in a scent storage slot 250. Each canister has a release valve (not shown) of well-understood, conventional construction. Multimedia information is stored in high density, two-dimensional bar codes 110". The two-dimensional bar codes 110" are also used to store scent identification and scent recovery sequence information to control the release of scents from the canisters 260.

The scent storage media and multimedia storage means described herein can be combined in various ways which are also within the scope of this invention. For example, scent canisters can be combined with other optical or magnetic multimedia storage formats.

II. Second Preferred Embodiment

Figure 5:
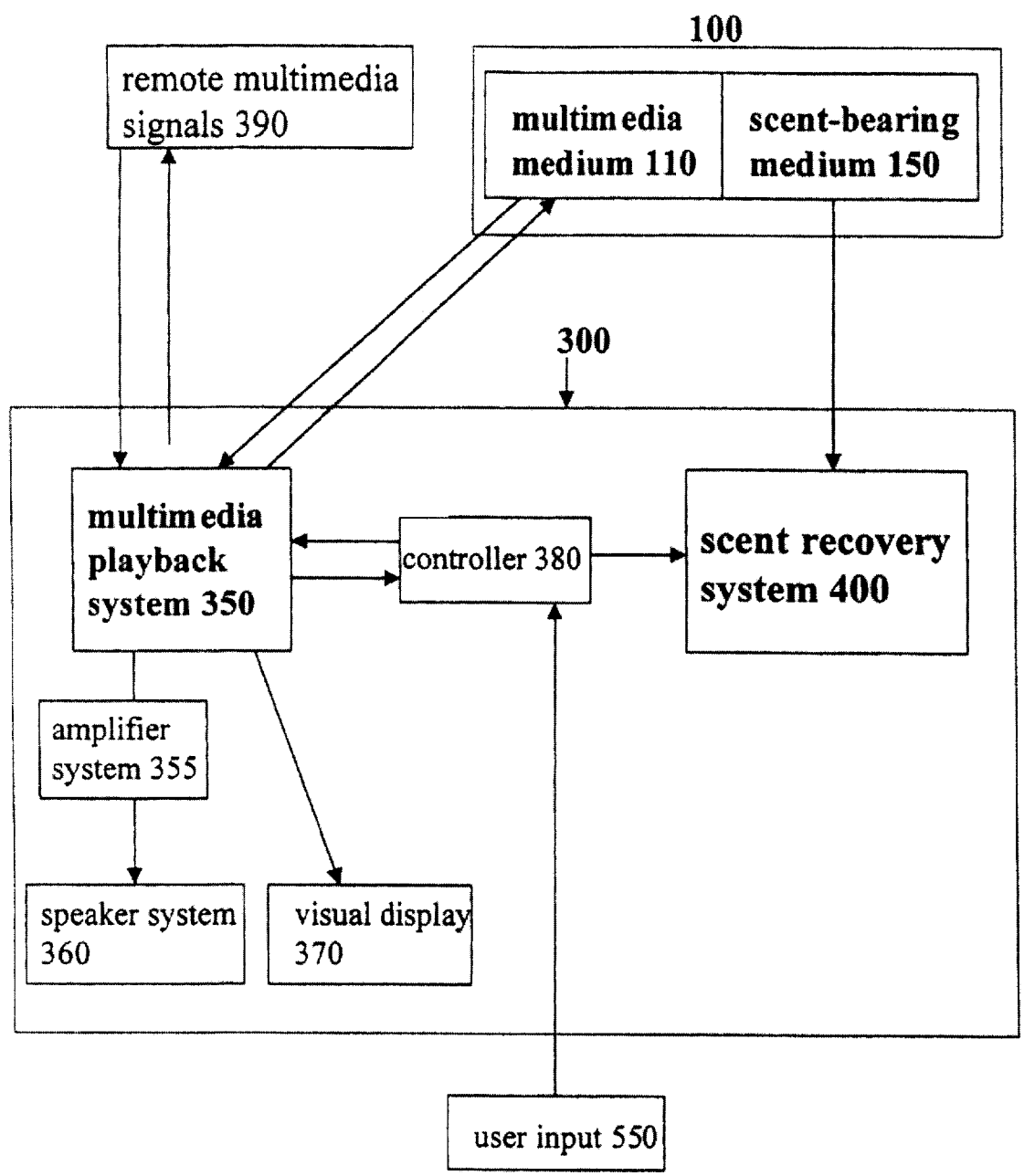
FIG. 5 depicts a conceptual block diagram showing an integrated system having a multimedia and scent storage medium and a multimedia playback and scent recovery system made in accordance with a second preferred embodiment of the present invention.
Figure 6:
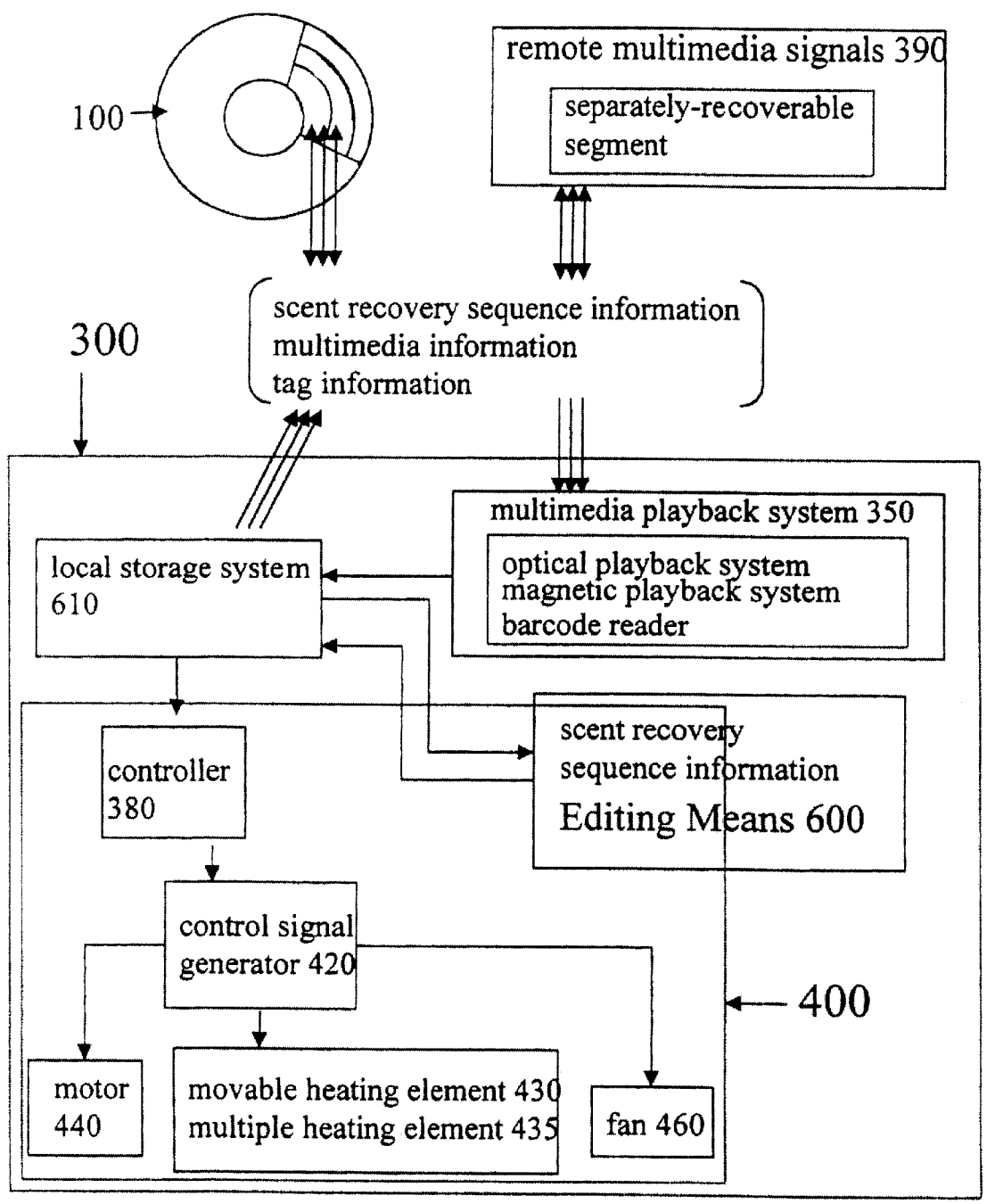
FIG. 6 depicts a conceptual block diagram of a scent recovery system 400 made in accordance with a second preferred embodiment of the present invention.

A second embodiment of the present invention comprises the combination of a multimedia and scent storage medium 100 and an integrated multimedia playback and scent recovery system 300 as shown in conceptual form in FIGS. 5 and 6. As in the case of the first embodiment, the multimedia and scent-bearing medium 100 of the second preferred embodiment comprises a multimedia storage medium 110 and a scent-bearing medium 150. The integrated multimedia playback and scent recovery system 300 comprises a multimedia playback system 350 and a scent recovery system 400. The multimedia playback system 350 recovers multimedia information from the multimedia storage medium 110. The multimedia playback system 350 converts audio information recovered from the multimedia storage medium 110 into an audio signal for amplification by an amplifier system 355 and for playback on a speaker system 360. Video information recovered from the multimedia storage medium 110 is converted into a video signal for playback on a video display 370.

The multimedia playback system 350 also recovers scent identification and scent recovery sequence information from the multimedia storage medium 110. This information is converted into a control signal by controller 380. The control signal generated by controller 380 is used to control the scent recovery system 400. Thus, the multimedia playback system 350 can be used to recover pre-programmed multimedia and scent recovery sequences stored on the multimedia and scent-bearing medium 100. In addition, the multimedia playback system 350 can also be used in or conjunction with remote multimedia signals 390 which may be recovered from various sources, e.g., radio/broadcasting, satellite, Internet, a public switched telephone network (PSTN), a LAN, a WAN or a computer. These remote multimedia signals 390 may also include scent recovery sequence information. Thus, scents stored in the multimedia and scent-bearing medium 100 can be used in the second preferred embodiment either with multimedia signals stored in the multimedia and scent-bearing medium 100 or with remote multimedia signals 390 captured from a plurality of sources.

Figure 7:
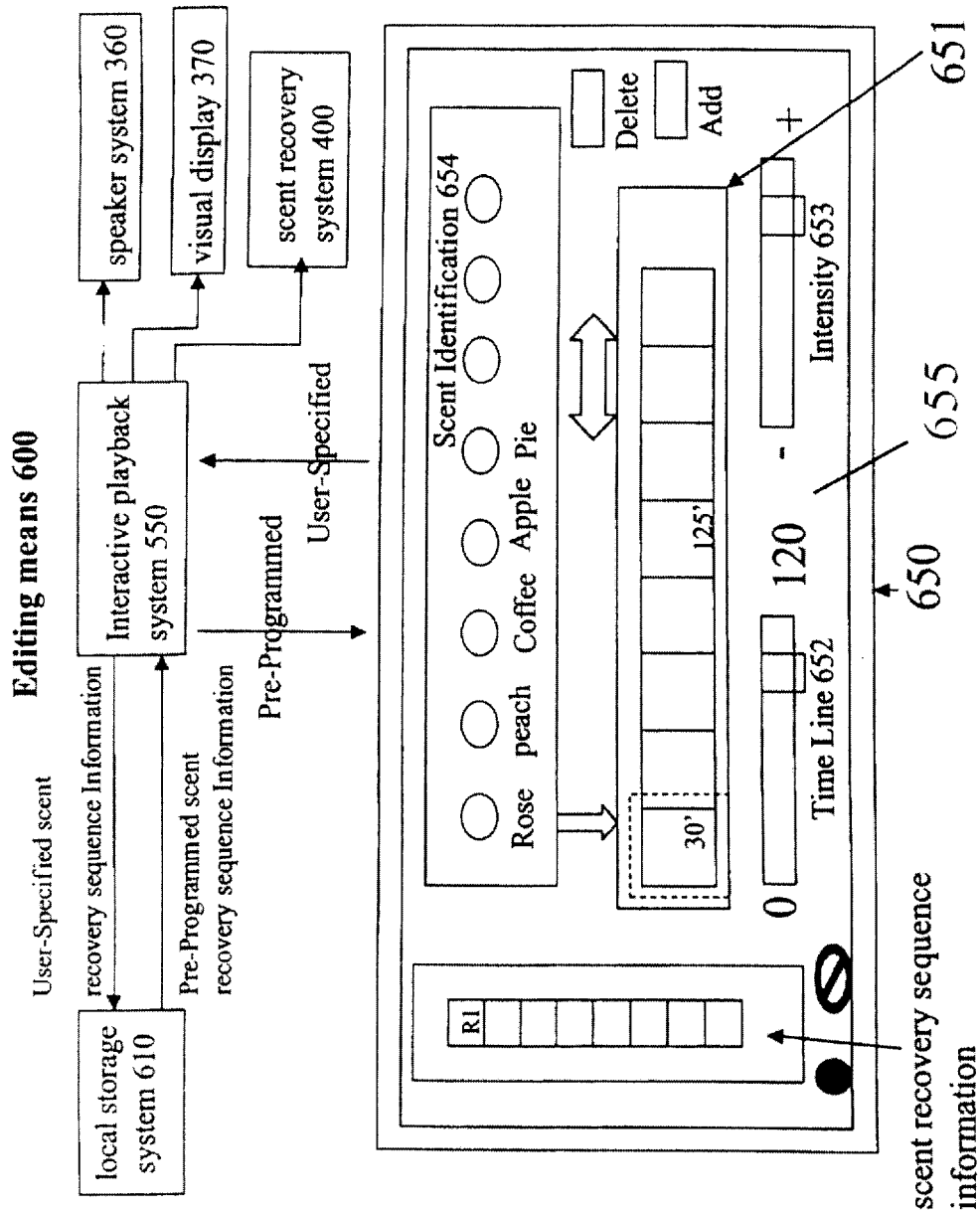
FIG. 7 depicts a conceptual block diagram illustrating editing means 600 and graphical user interface 650 intended for operation in accordance with a second preferred embodiment of the present invention.

The multimedia playback and scent recovery system 300 has several playback modes. For example, a user could simply "play back" pre-programmed multimedia and synchronized scent recovery sequences by depressing a start button to initiate the sequence. The multimedia playback and scent recovery system 300 also facilitates other playback modes. For example, the multimedia playback and scent recovery system 300 also includes as part of the interactive playback system 550 an editing means 600 as shown in FIGS. 6 and 7 for "customizing" pre-programmed multimedia and scent recovery sequences to accommodate user preferences. The editing means 600 comprises a local storage system 610 for storing the scent recovery sequence information recovered either from the multimedia and scent-bearing 100 or the remote source 390. Many types of local storage systems 610 may be used to store multimedia information, for example, a mini hard drive, a RAM, or a MP3.

The editing means 600 also comprises a graphical user interface 650 which is depicted in FIG. 7 and which may be displayed on the display system of the multimedia playback and scent recovery system 300. The graphical user interface 650 as depicted in FIG. 7 may take many forms within the scope of this invention. For example, the graphical user interface 650 may include a portion 651 that depicts in graphical form the multimedia segments for which scent recovery sequence information is created. The scent recovery sequence information will be edited on a multimedia segment by segment basis. The user would double click on which multimedia portion indicated in 651 he/she wishes to edit the pre-programmed scent recovery sequence information. Once the user has indicated the multimedia segment of interest, the editing means 600 will recall the scent recovery sequence information corresponding to the segment from memory and display it in region 651. The display in region 651 will comprise a combination of timeline 652, intensity 653 and scent identification information 654. The timeline 652 will indicate which scents will be recovered in what sequence, and for what duration. The intensity segment 653 effectively specifies the amount of heat that will be applied to the scent-bearing regions 151 of the multimedia and scent-bearing medium 100.

A Java platform, particularly its Abstract Windowing Toolkit (AWT) can be used to create custom graphical front ends 655 for display on the graphical user interface 650. The AWT provides interfaces and classes for dealing With different types of events generated by AWT components. In addition, Java gives application programmers numerous tools for building professional, customizable cross-platform GUIs (graphic user interface).

Alternatively, the graphical user interface 650 can be created using a "Windows" platform. The coded Application Interface (API) can be used to create custom graphical front ends. Some C++ applications already provide interfaces and classes for dealing with different types of events generated by API components.

The editing means 600 through the graphical user interface 650 permits a user to add scents, delete scents, overlap scents, increase the duration of scents, and decrease the duration of scents. Further, the editing means 600 permits a user to create an entirely new scent recovery sequence for use with multimedia segments.

Figure 8:
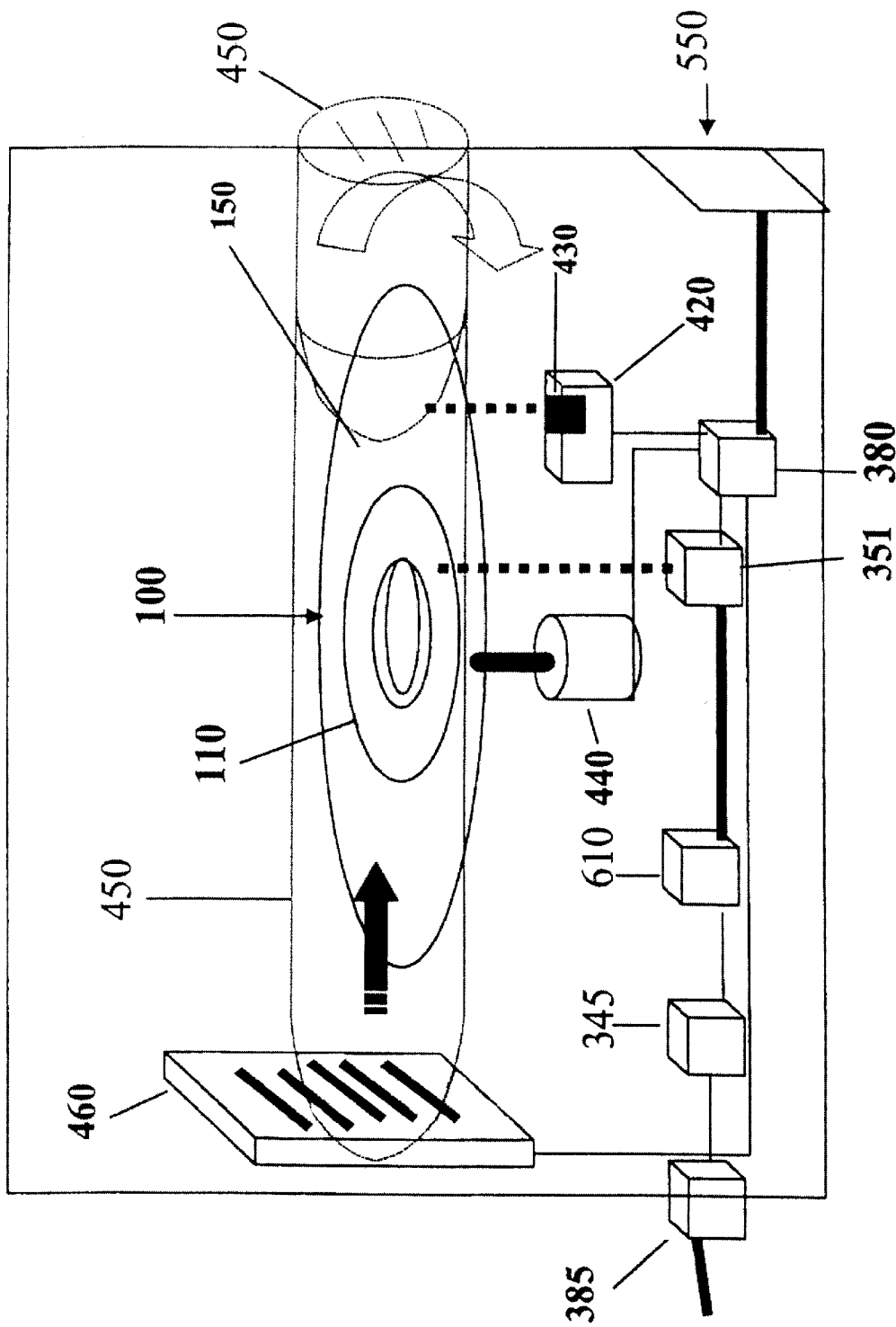
FIG. 8 depicts a schematic cross-sectional side view of a scent recovery system 400 made in accordance with a second preferred embodiment of the present invention for use in combination with multimedia and scent-bearing medium 100.

A cross-sectional side view of the scent recovery system 400 in accordance with a preferred second embodiment of the present invention is illustrated in FIG. 8. The scent recovery system 400 includes a movable heating element 430 (e.g. an Infrared or laser) which operates in response to control signals provided by the control signal generator 420 (e.g. Motorola's 8000 series microprocessor). After recovery of the scent recovery sequence information, tag information, and multimedia information from the multimedia storage medium 10 to the local storage system 610, the controller 380 (e.g. CMOS PIC microcontroller) can use the tag information as reference data to couple event-related scent recovery signals which either have been transmitted from a remote multimedia source 390 or from the multimedia storage medium 110 to emit a predetermined scent or combination of scents from the scent disk 100 by a ductwork 450 and controlled fan 460 (e.g. heat sink fan). A replaceable scent disk 100 emits a predetermined scent or a combination of scents when heated. Preferably, a predetermined scent from a scent-bearing medium 150 from the scent disk 100 is positioned directly above and/or in front of the movable heating element 430 by a controlled motor 440 (e.g. bipolar stepper motor).

Figure 9:
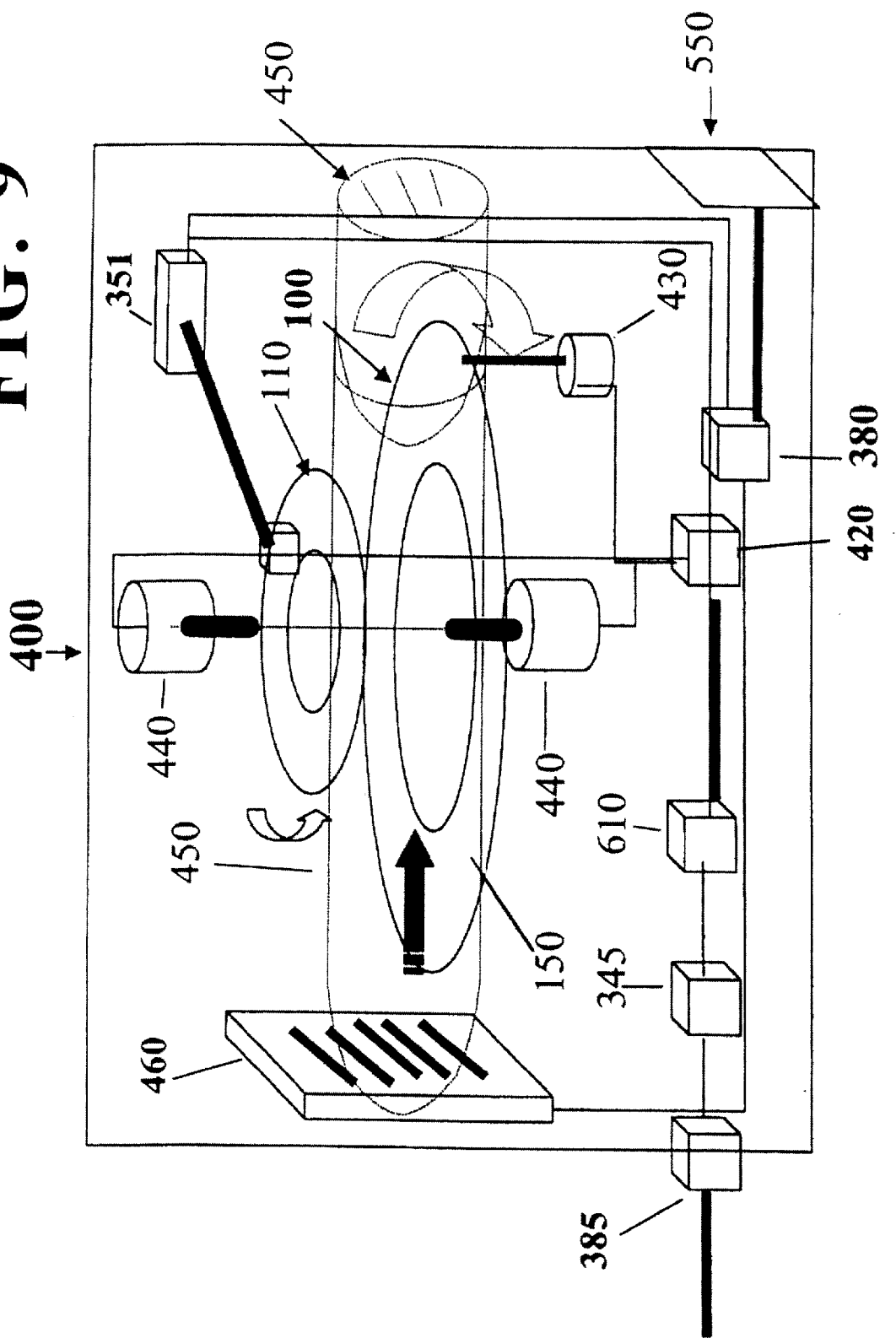
FIG. 9 depicts a schematic cross-sectional side view of an alternate scent recovery system 400 made in accordance with a second preferred embodiment of the present invention for use in combination with an alternate multimedia and scent-bearing medium 100.

In another preferred first and second embodiment of this invention shown in FIG. 9, a separable multimedia storage medium 110 (e.g. a compact disc) from scent-bearing medium 150 can actually operate as a separate entity by separate selectively controlled motor 440 without interruption to either unit.

Figure 10:
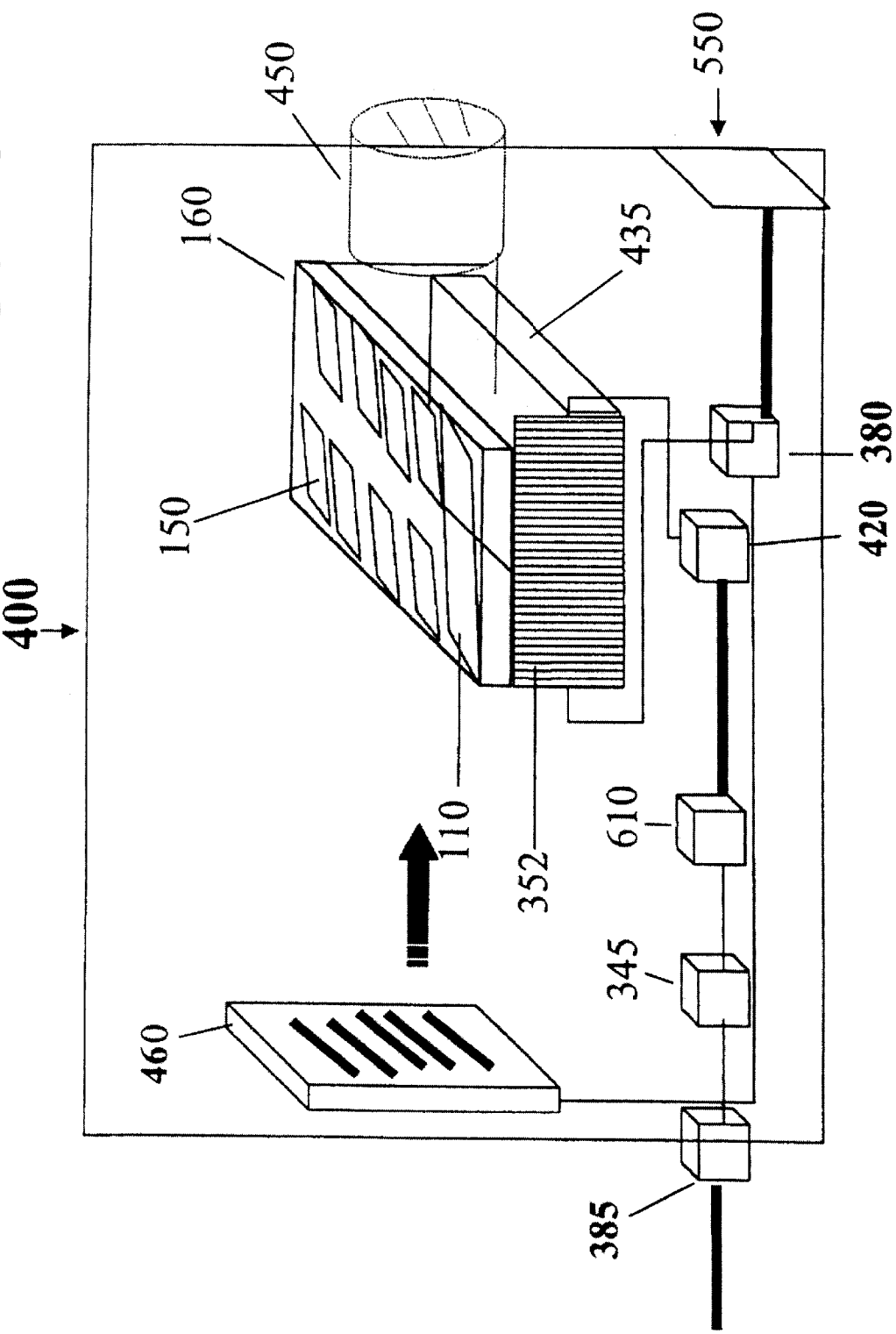
FIG. 10 depicts a schematic cross-sectional side view of an alternate scent recovery system 400 made in accordance with a second preferred embodiment of the present invention for use in combination with an alternate multimedia and scent-bearing medium 160.

Yet another cross-sectional side view of a scent recovery system 400 in accordance with a preferred second embodiment of the present invention is illustrated in FIG. 10. The scent recovery system 400 includes a multiple heating element 435 (e.g. an infrared or laser heating coil) which operates in response to control signals provided by the control signal generator 420. The insertable scent card 160 electronically connects with the controller 380 through a connector type magnetic playback system 352. After recovery of the scent recovery sequence information, tag information, and multimedia information from the multimedia storage medium 110 to the local storage system 610, the controller 380 can use the tag information as reference data to couple event-related scent recovery signals which either have been transmitted from a remote multimedia source 390 or from the multimedia storage medium 110 to emit predetermined scent or combination of scents from the scent card 160 by a ductwork 450 and controlled fan 460. A replaceable scent card 160 emits a predetermined scent or combination scents of scents when heated. Preferably, a pre-determined scent from a scent-bearing medium 150 from the scent card 60 is positioned directly above and/or in front of the multiple heating element 435 by selective control signals.

Figure 11:
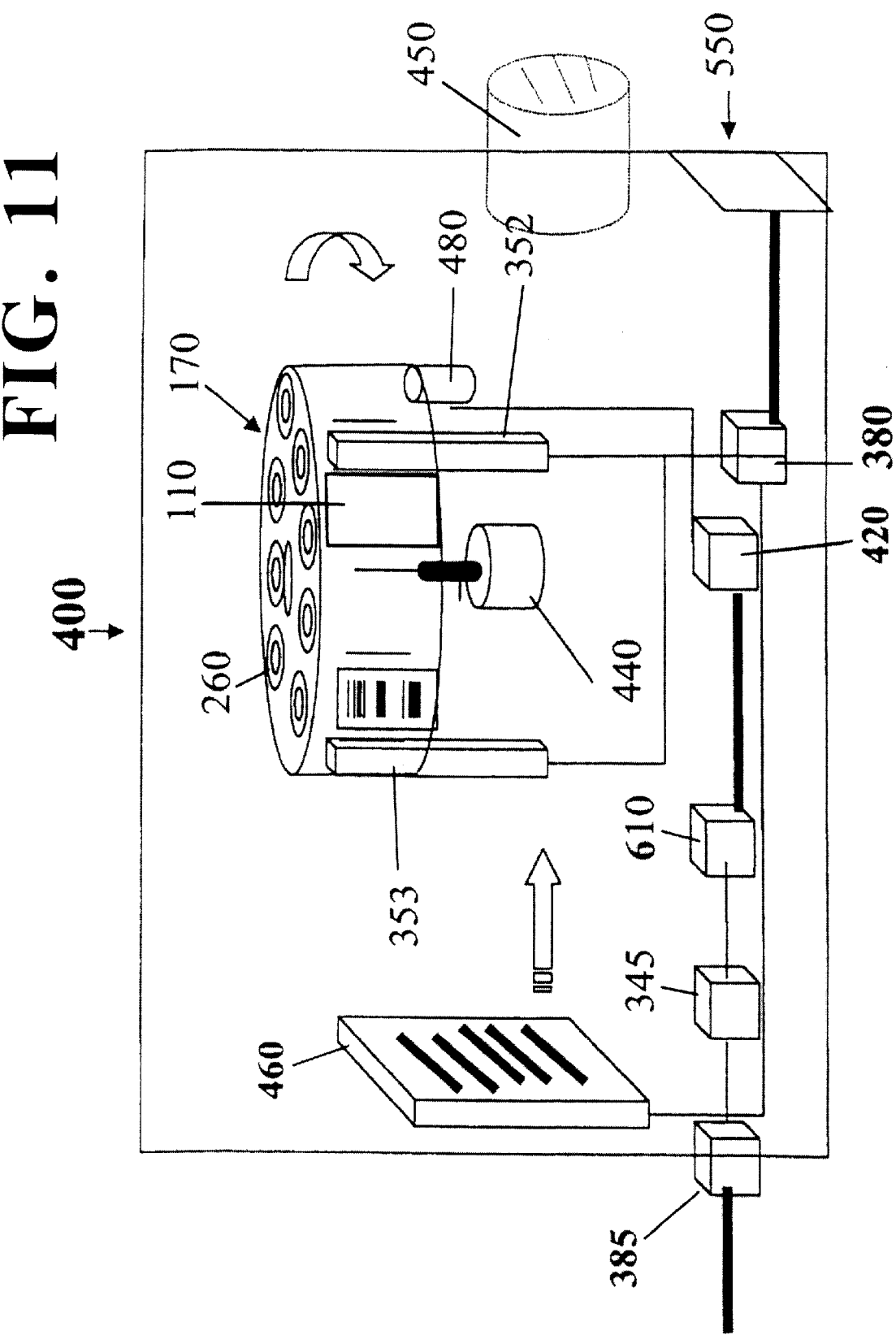
FIG. 11 depicts a schematic cross-sectional side view of an alternate scent recovery system 400 made in accordance with a second preferred embodiment of the present invention for use in combination with an alternate multimedia and scent-bearing medium 170.

A cross-sectional side view of a scent recovery system 400 in accordance with a preferred second embodiment of the present invention is illustrated in FIG. 11. The scent recovery system 400 includes a selectively controlled release valve system 480 (e.g. an ink-jet system) which operates in response to control signals provided by the control signal generator 420. A barcode reader 353 or magnetic playback system 352 will retrieve the scent recovery sequence information, tag information, and multimedia information from the scent identification 120 or multimedia storage medium 110 into the local storage system 610, the controller 380 can use the tag information as reference data to couple event-related scent recovery signals which either have been transmitted from a remote multimedia source 390 or from the multimedia storage medium 110 to emit predetermined scent or combination of scents from the cartridge 170 by a ductwork 450 and controlled fan 460. The replaceable scent cartridge 170 emits a predetermined scent or a combination of scents when activated. Preferably, a predetermined scent from a canister 260 from the scent cartridge 170 is positioned directly in front of the ductwork 450 and controlled fan 460 by a controlled motor 440.

Figure 12:
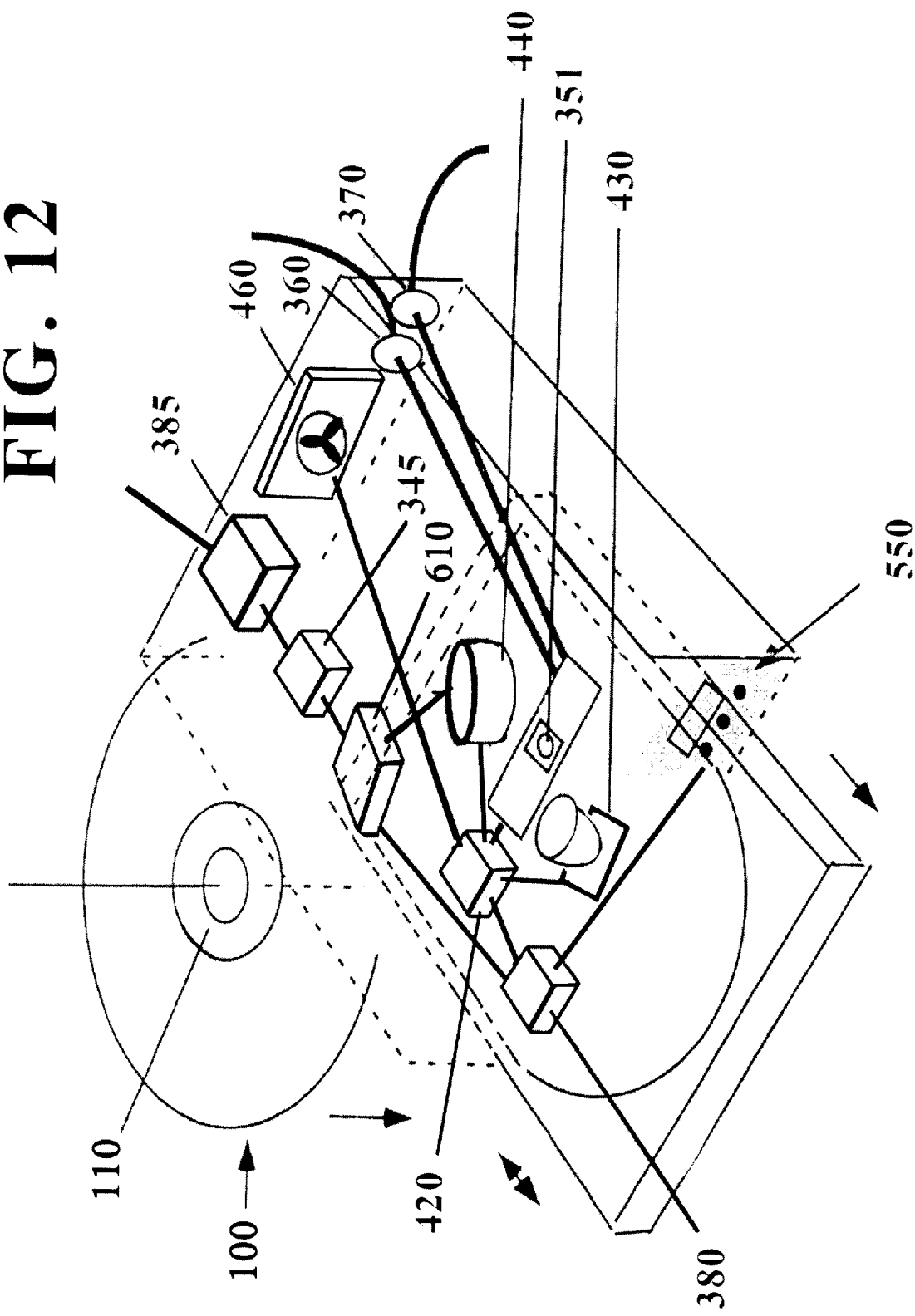
FIG. 12 depicts an exploded view of a multimedia playback and scent recovery system made in accordance with a second preferred embodiment of the present invention for use in combination with a multimedia and scent-bearing medium 100.
Figure 13:
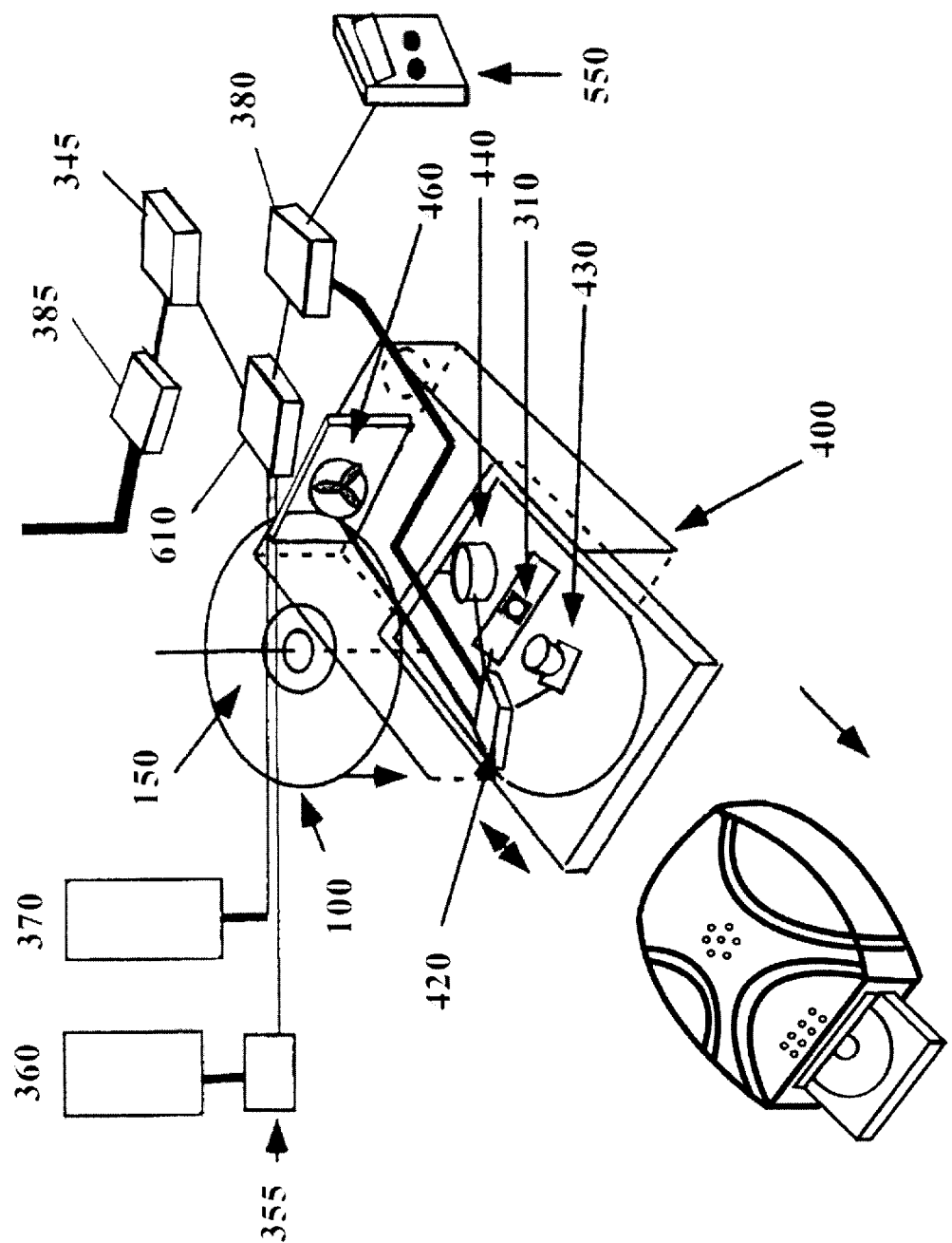
FIG. 13 depicts an exploded view of an alternate multimedia playback and scent recovery system made in accordance with a second preferred embodiment of the present invention for use in combination with an alternate multimedia and scent-bearing medium 100.

A multimedia playback and scent recovery system according to a preferred embodiment of the present invention is illustrated in FIG. 12. In this embodiment, the playback system comprises a scent disk. 106 having not only a scent-bearing medium 150 but also a multimedia storage medium 110 (e.g. a compact disc), with scent recovery sequence information, tag information, and multimedia information encoded thereon. A multimedia playback system 350 including an optical playback system 351 serves as the recovery system for accessing and processing the scent recovery sequence information; tag information, and multimedia information stored on the multimedia storage medium 110. The optical playback system 351 transmits scent recovery sequence information, tag information, and multimedia information to the controller 380 which encodes scent recovery sequence information into electronic signals prior to transmitting to the scent recovery system 400 or to a local storage system 610. A control signal generator 420 then retrieves the electronic signals to the scent recovery system 400.

Figure 14:
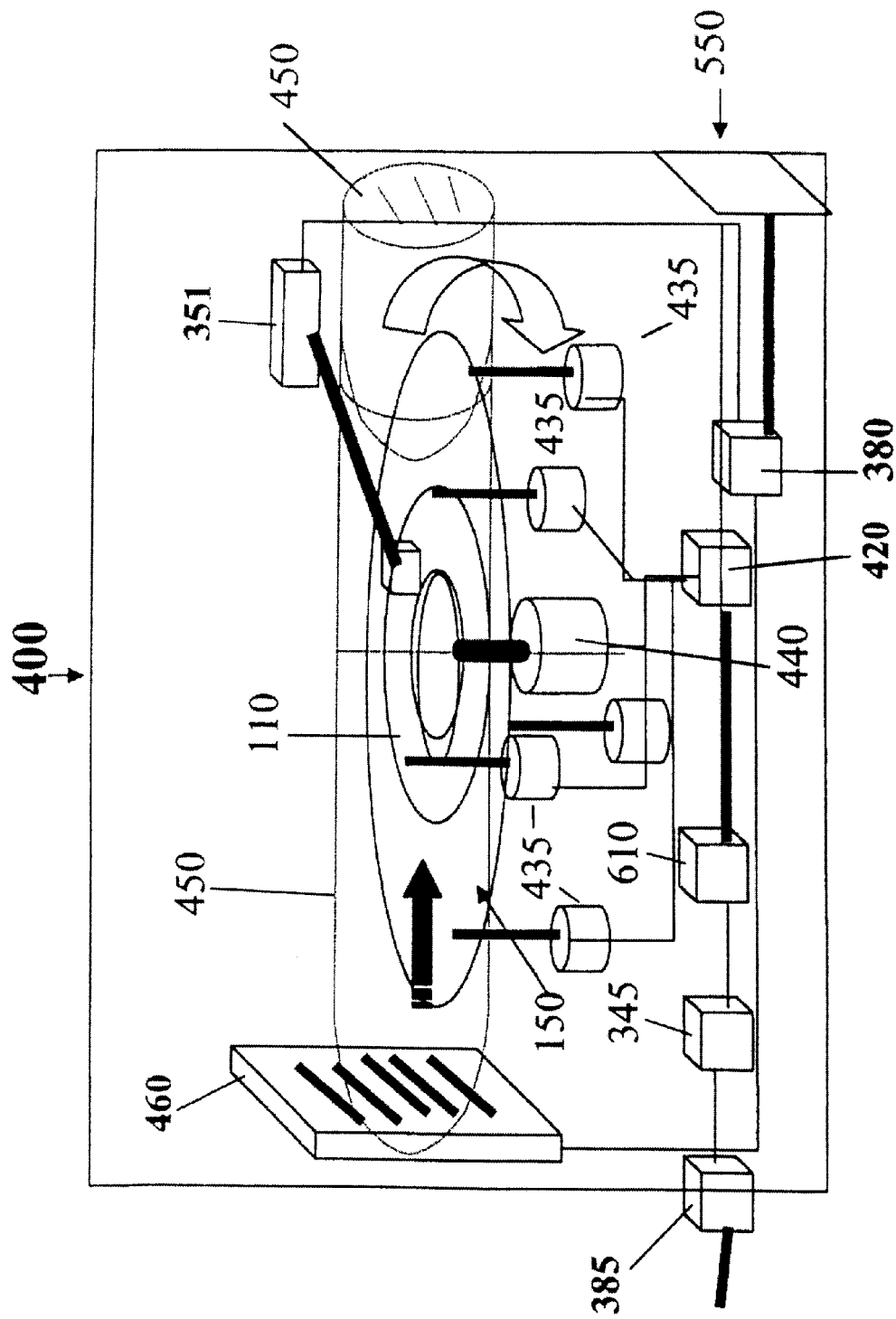
FIG. 14 depicts a schematic cross-sectional side view of an alternate scent recovery system 400 made in accordance with a second preferred embodiment of the present invention for use in combination w a alternate multimedia and scent-bearing medium 100.

A cross-sectional side view of a scent recovery system 400 in accordance with a preferred second embodiment of the present invention is illustrated in FIG. 14. The scent recovery system 400 includes a multiple heating element 435 (e.g. an Infrared or laser heating coil) which operates in response to control signals provided by the control signal generator 420. After recovery of the scent recovery sequence information, tag information, and multimedia information from the multimedia storage medium 110 to the local storage system 610, the controller 380 can use the tag information as reference data to couple event-related scent recovery signals which either have been transmitted from a remote multimedia source 390 or from the multimedia storage medium 110 to emit predetermined scent or combination of scents from the scent disk 100 by a ductwork 450 and controlled fan 460. A replaceable scent disk 100 emits a predetermined scent or combination of scents when heated.

Preferably, a plurality of predetermined scents from a scent-bearing medium 150 from the scent disk 100 are positioned directly above and/or in front of the multiple heating element 435 by selective control signals.

Figure 15:
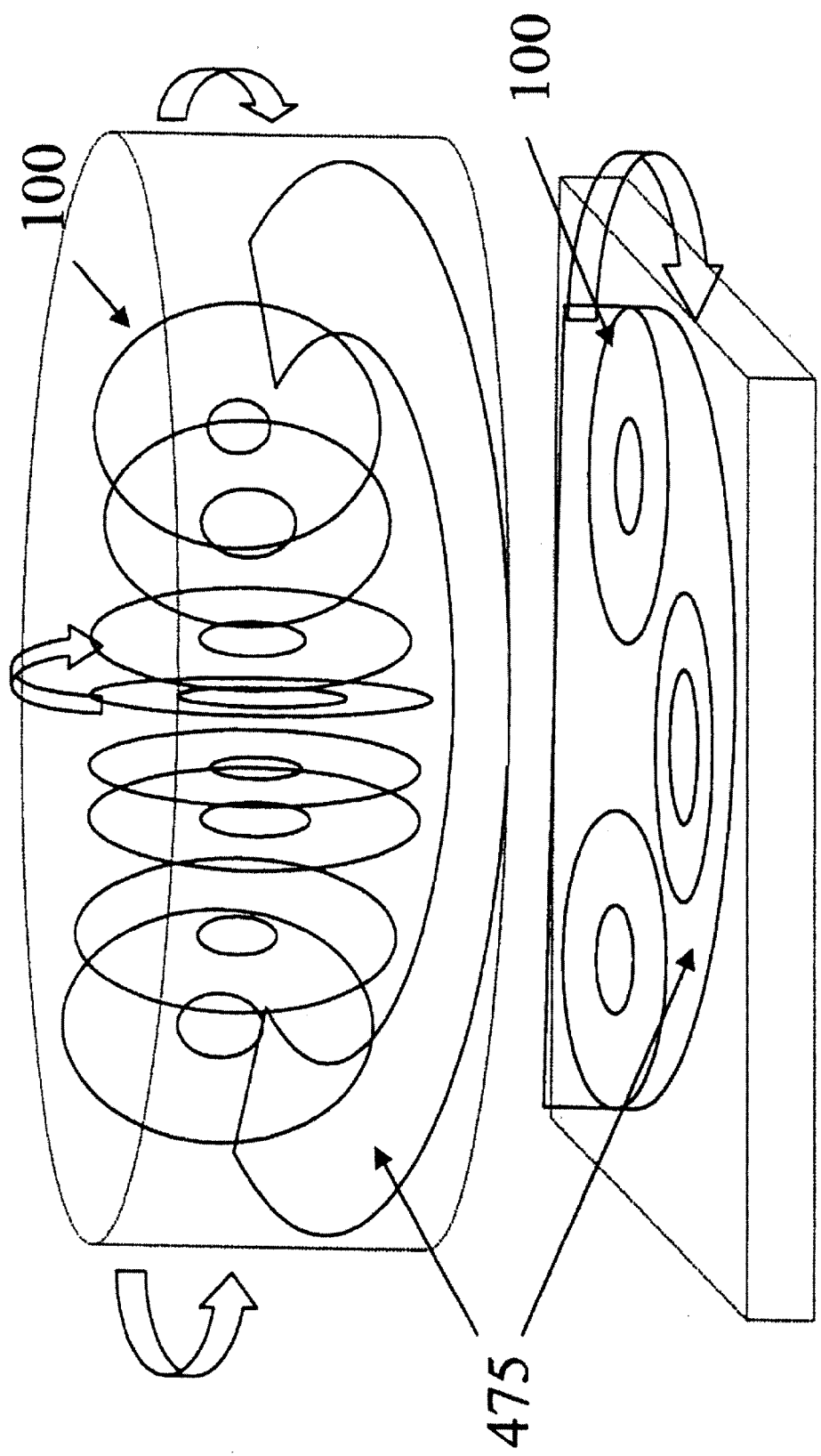
FIG. 15 depicts a cross-sectional view of an alternate multimedia playback and scent recovery system made in accordance with a second preferred embodiment of the present invention for use in combination with an alternate multimedia and scent-bearing medium 100.

Another preferred embodiment of this invention is shown in FIG. 15, with the advantage of the scent recovery sequence information and multimedia information therein, illustrates another version of a multimedia playback and scent recovery system according to a preferred embodiment of the present invention by loading multiple scent disks 100 in the disk-like slots 475 within a jukebox-like embodiment.

Figure 16:
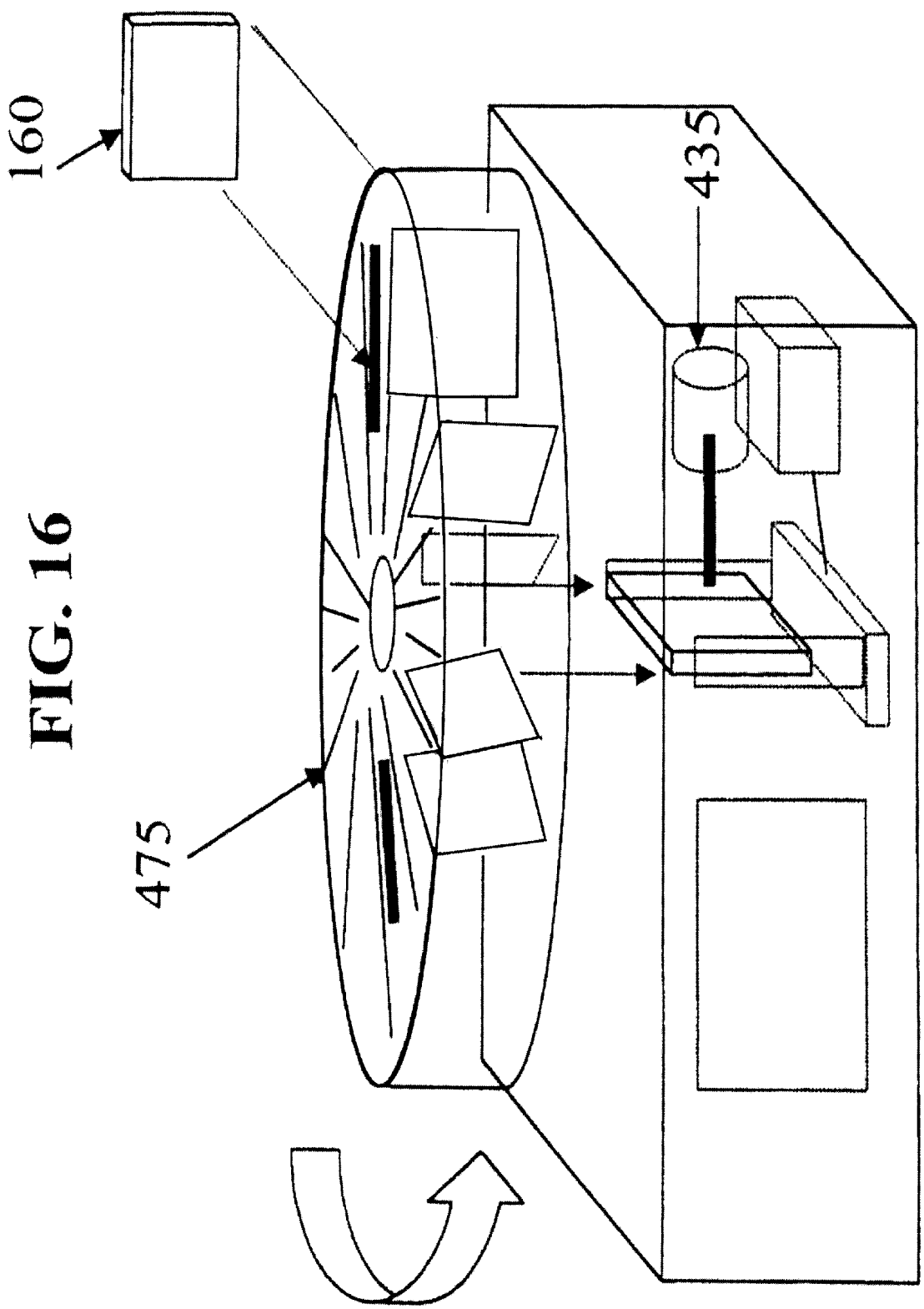
FIG. 16 depicts a cross-sectional view of an alternate multimedia playback and scent recovery system made in accordance with a second preferred embodiment of the present invention for use in combination with an alternate multimedia and scent-bearing medium 160.

Another preferred embodiment of this invention shown in FIG. 16, with the advantage of the scent recovery sequence information and multimedia information therein, illustrates another version of a multimedia playback and scent recovery system according to a preferred embodiment of the present invention by loading multiple scent cards 160 on card-like slots 475 within a slide projector-like embodiment.

In operation, the multimedia playback system 350 recovers at least the tag information and/or a portion of the scent recovery sequence and multimedia information encoded on the multimedia storage medium 110 or from a remote multimedia source 390 through the input connection 385. The multimedia playback system 350 then transmits electronic signals to the controller 380 to generate scent control signals coupled with the tag information from the multimedia storage medium 110. Upon receipt of the control signals from the control signal generator 420, the controlled motor 440 that turns the scent disk 100, the movable heating element 430, and the controlled fan 460 are activated, thereby releasing the desired scent or combination of scents. The movable heating element 430 and the controlled fan 460 may be activated for an identical period of time, or for different lengths of time to release different strengths of their respective scents. In addition, the movable heating element 430 (e.g. infrared or laser) only targets heat-releasable scents 230 within the inert storage medium 152 on the scent disk 100. The inert storage medium 152 will not interfere with the heat absorption process. Each of the systems in the scent recovery system 400 is deactivated in response to control signals transmitted by the control signal generator 420 to prevent any further scent release. When deactivated, the controlled motor 440, the movable heating element 430, the controlled fan 460 are turned off. This process is repeated, as necessary, according to the scent recovery sequence and multimedia information encoded on the multimedia storage medium 110.

III. Third Preferred Embodiment

A third preferred embodiment of the present invention is depicted generally in FIGS. 17–25. FIGS. 17–20 and 25 depict top views, a side view and a bottom view of a multimedia playback and scent recovery system 700 and multimedia and scent storage disc 100 made in accordance with the present invention. The multimedia playback and scent recovery system 700 comprises a semicircular housing 701 for enclosing the multimedia playback means, scent recovery means and interfacing means. The multimedia playback and scent recovery system 700 has a top surface 710, side surface 730 and a bottom surface 740. The multimedia playback and scent recovery system 700 has in its upper surface 710 a plurality of vents 711 for permitting scents released from the multimedia and scent storage disc 100 by the scent recovery means to be dispersed into the atmosphere. Also mounted in the upper surface 710 of the multimedia playback and scent recovery system are a plurality of control buttons 712 that partially comprise the user input and control means. Although five buttons 712 are shown in the FIGS., other combinations of buttons may be used. These buttons permit a user, for example, either to start multimedia playback and scent recovery, or pause multimedia playback and scent recovery, or to stop multimedia and scent recovery. Other functions may be implemented. For example, a button may be used to recover specific scents, or combinations of button entries may be used to program a new multimedia and scent recovery sequence. In variations of the third preferred embodiment, a liquid crystal display screen or other suitable display technology (not shown) may be included in the upper surface 710 to facilitate the user in monitoring the progress of playback or in programming the multimedia playback and scent recovery system 700.

Figure 17:
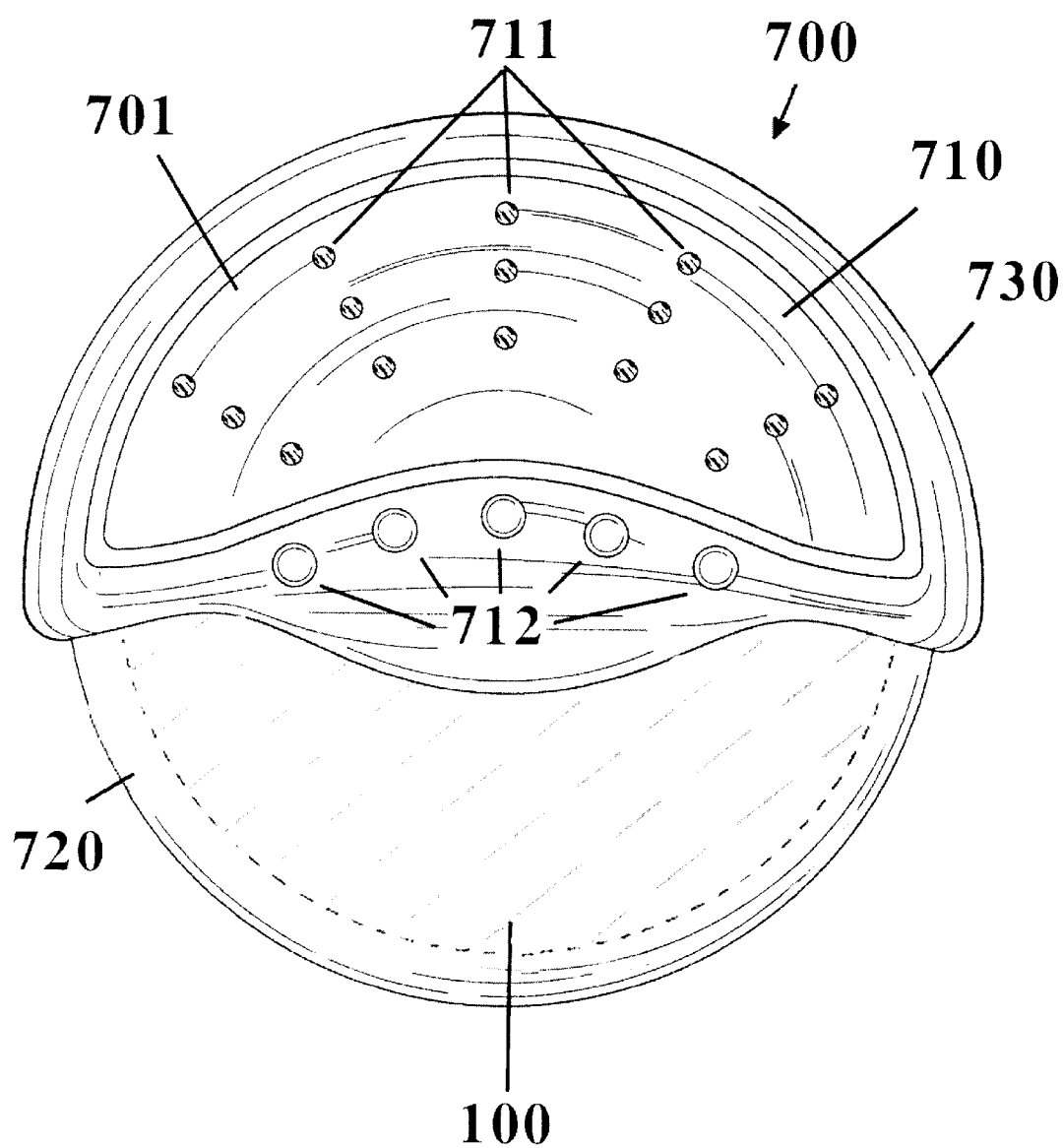
FIG. 17 depicts a top view of a multimedia playback and scent recovery system (with a retractable shield fully extended) and a multimedia and scent storage disc made in accordance with a third preferred embodiment of the present invention.
Figure 18:
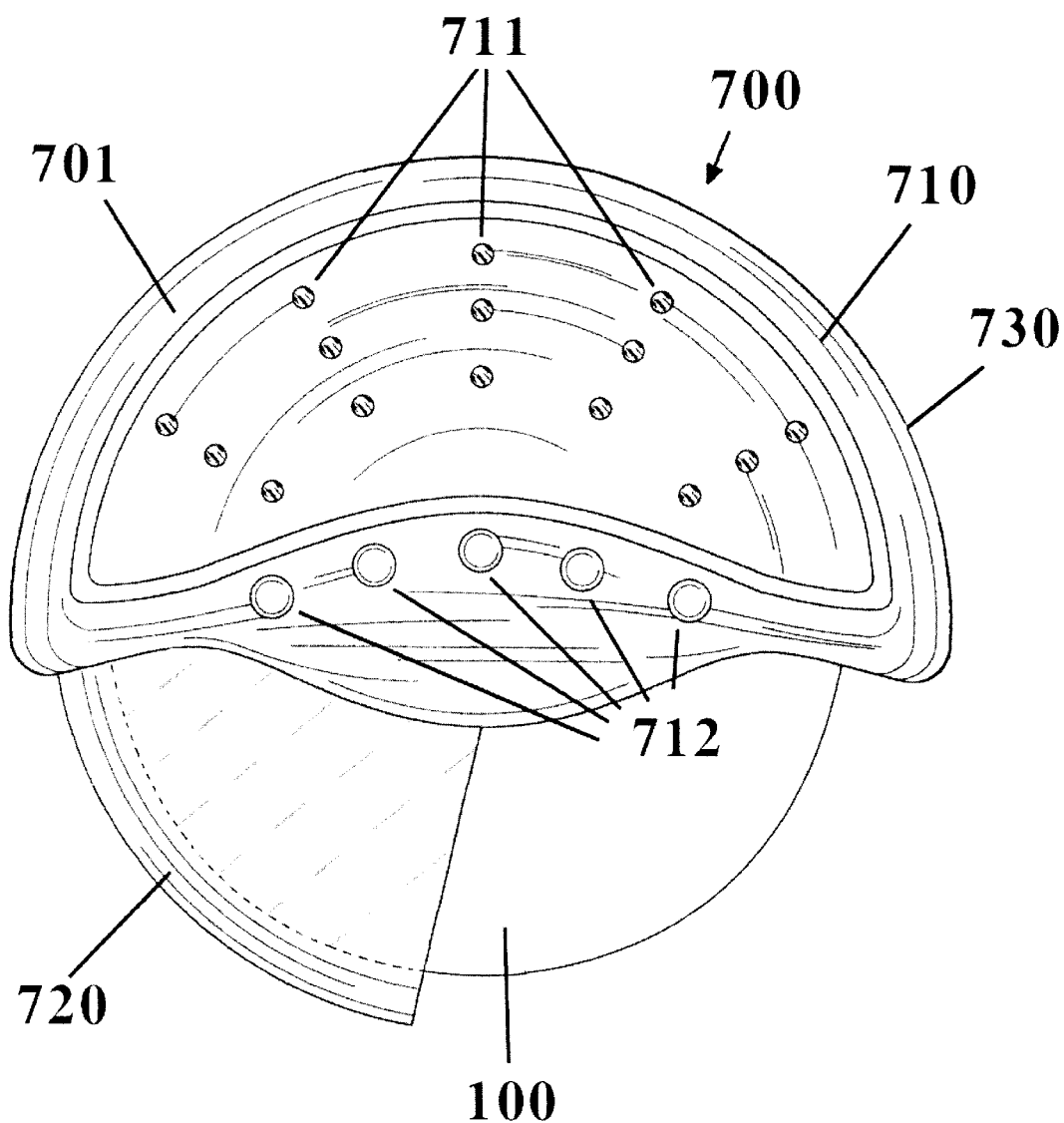
FIG. 18 depicts a top view of a multimedia playback and scent recovery system (with a retractable shield partially extended) and a multimedia and scent storage disc made in accordance with a third preferred embodiment of the present invention.
Figure 19:
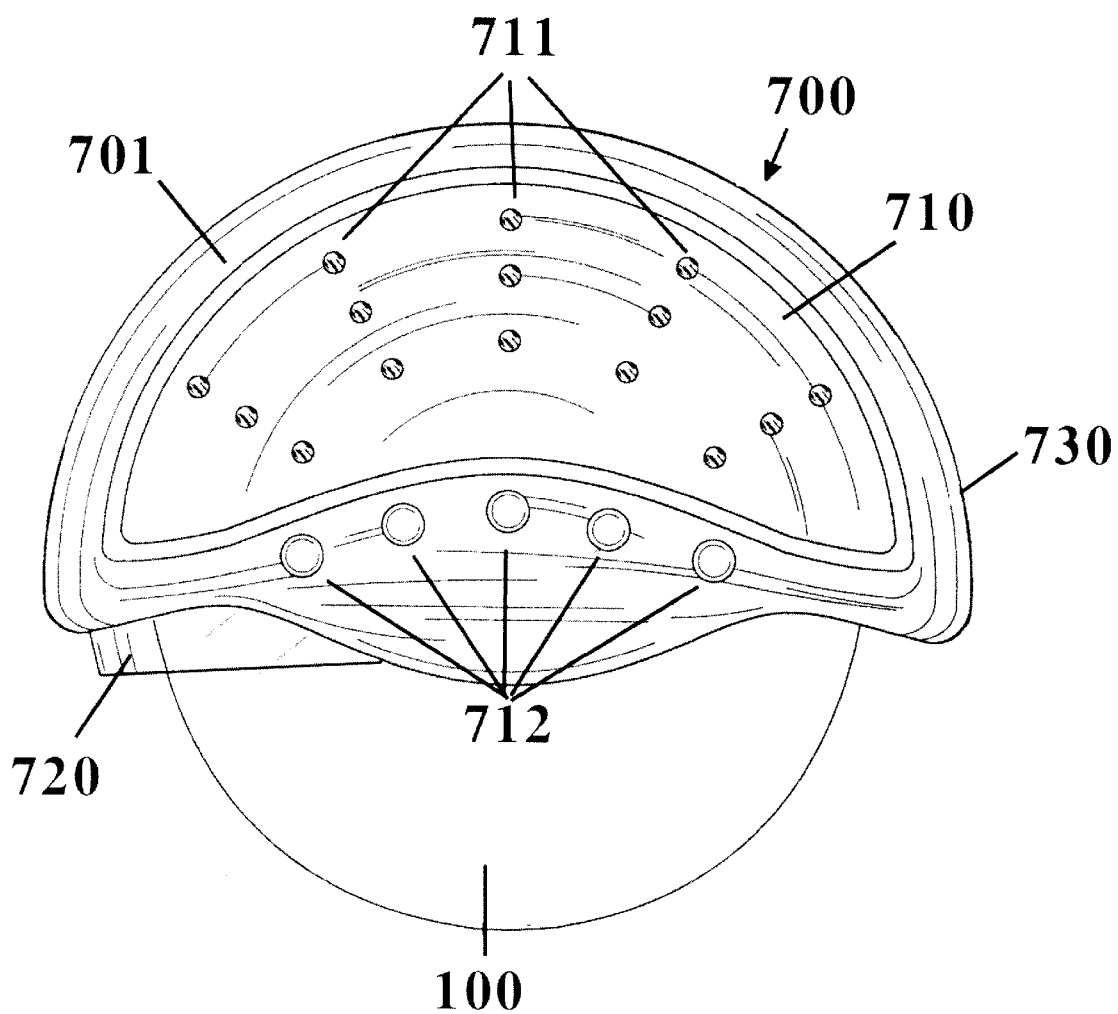
FIG. 19 depicts a top view of a multimedia playback and scent recovery system (with a retractable shield partially extended) and a multimedia and scent storage disc made in accordance with a third preferred embodiment of the present invention.
Figure 20:
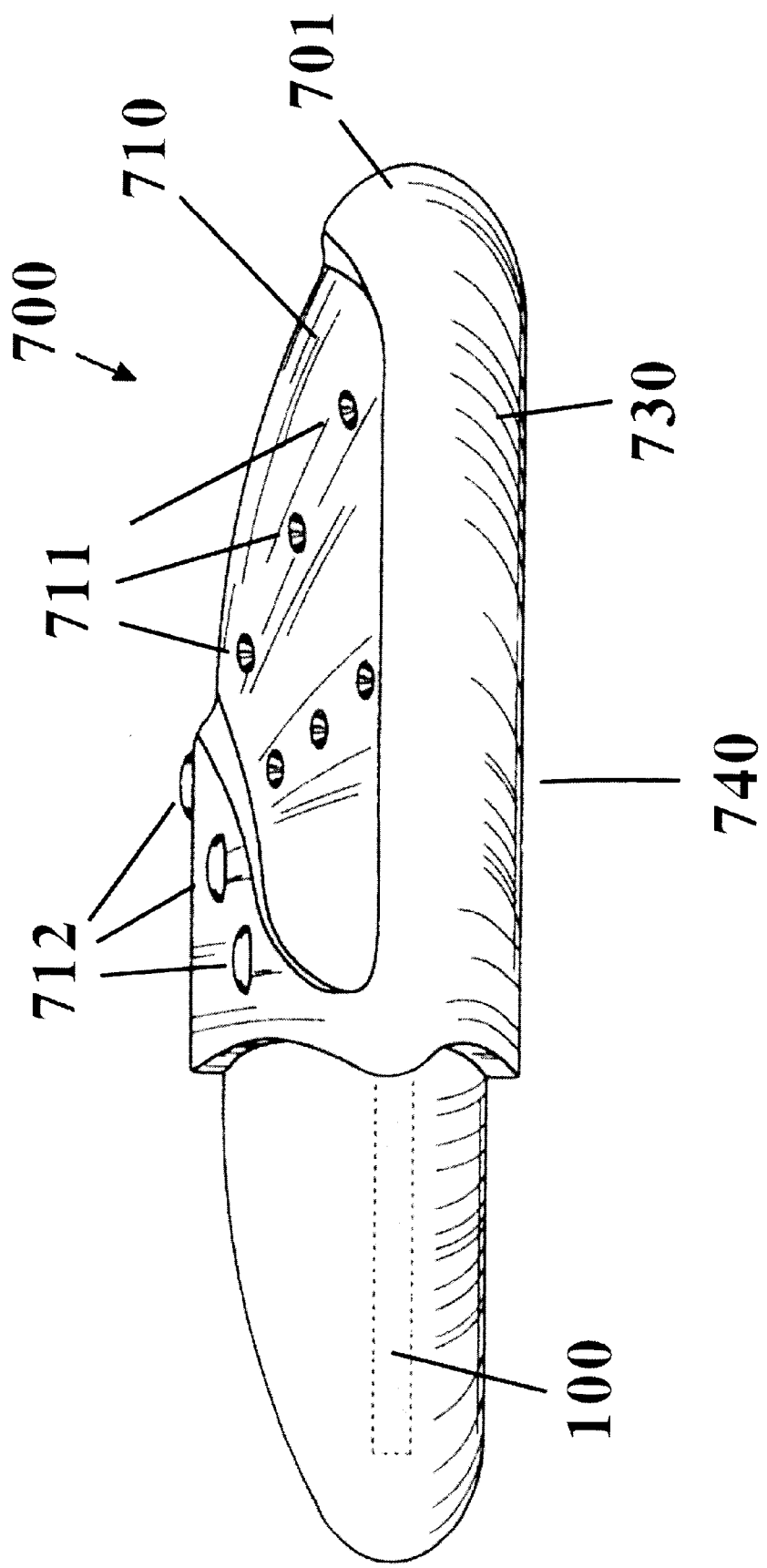
FIG. 20 depicts a side view of a multimedia playback and scent recovery system (with a retractable shield extended) and a multimedia and scent storage disc made in accordance with a third preferred embodiment of the present invention.

As depicted in FIGS. 17–19, the multimedia playback and scent recovery system 700 also comprises a retractable semicircular shield 720 for protecting the multimedia and scent storage disc 100 from damage while in use. The user would slide the retractable semicircular shield 720 as shown in FIGS. 18–19 to remove or insert a multimedia and scent storage disk. In variations of the third preferred embodiment, the retractable shield may be motor-driven, in which case a user would control the position of the retractable shield either by using a push-button, or by a pressure-sensitive switch that upon sensing slight movement of the retractable shield would fully retract or close the shield. The retractable shield 720 may be made from plastic or other suitable materials known to those skilled in the art. In various embodiments the shield may be transparent, translucent or opaque.

Figure 21:
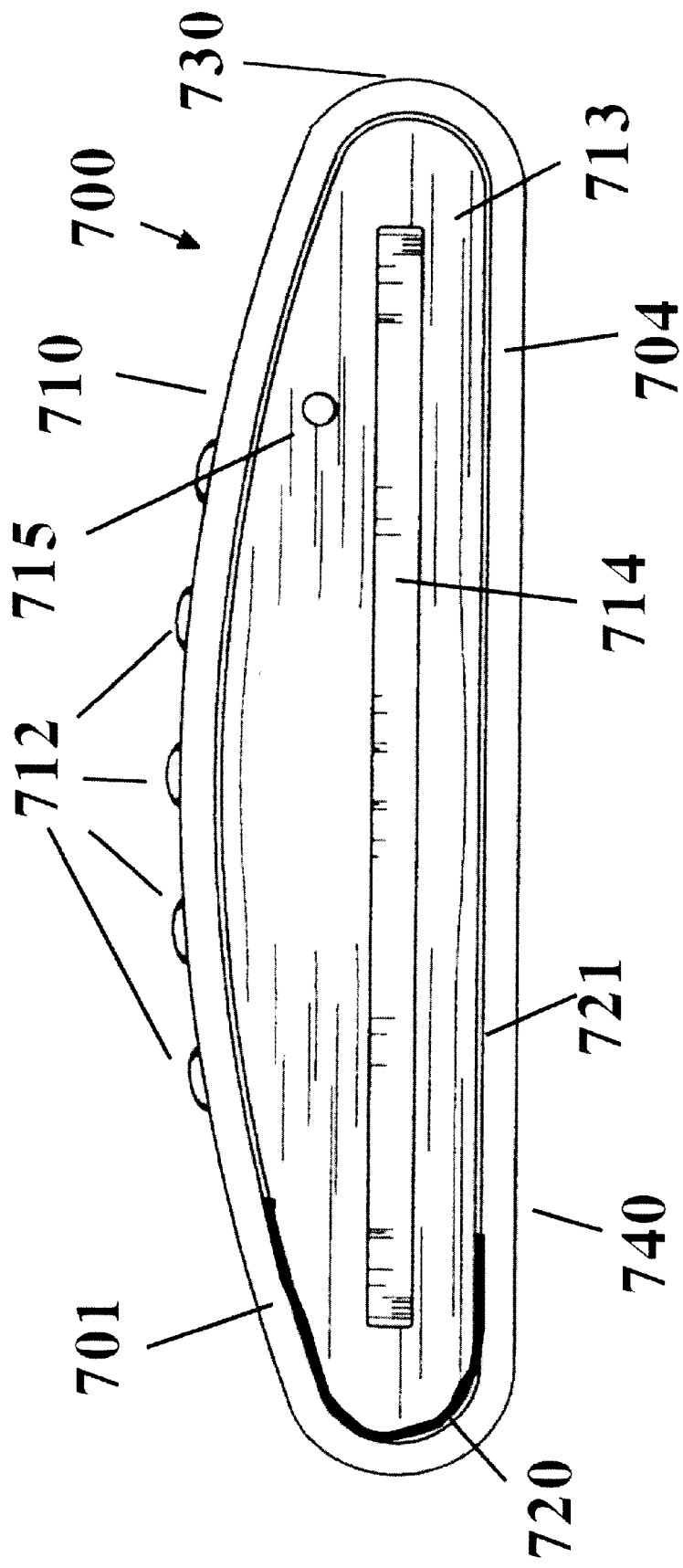
FIG. 21 depicts a front view of a multimedia playback and scent recovery system made in accordance with a third preferred embodiment of the present invention.
Figure 22:
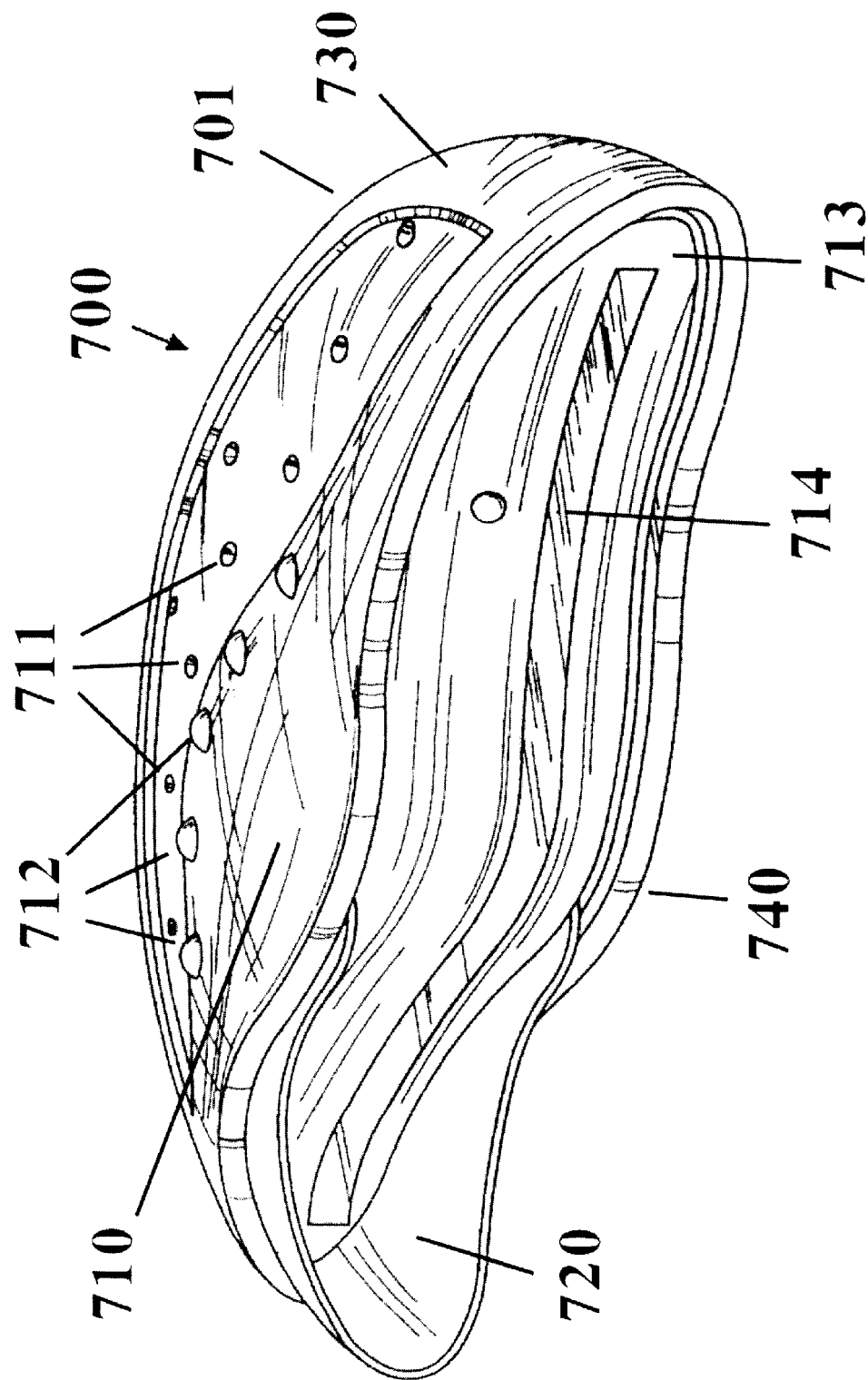
FIG. 22 depicts a front perspective view of a multimedia playback and scent recovery system made in accordance with a third preferred embodiment of the present invention.
Figure 23:
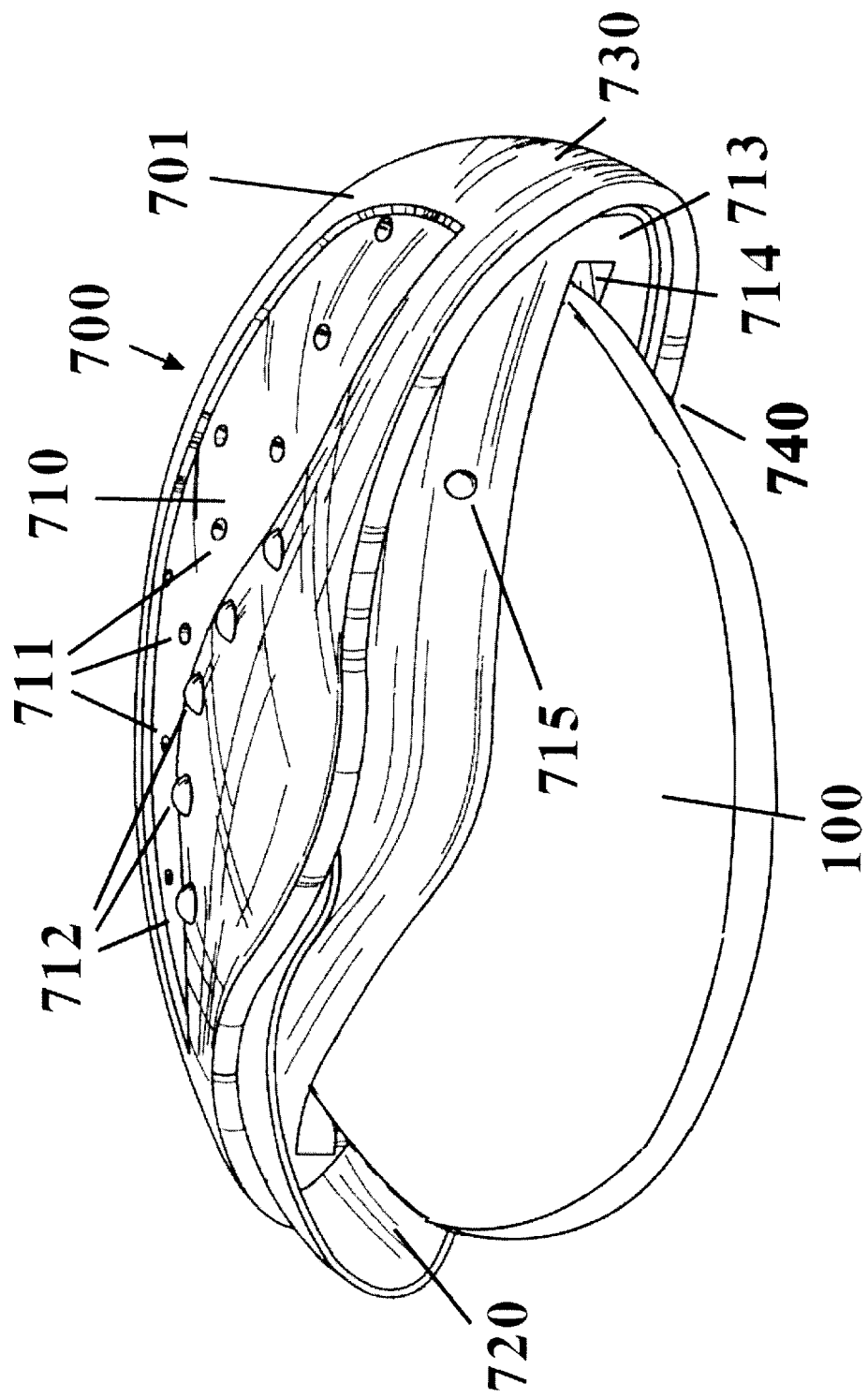
FIG. 23 depicts a front perspective view of a multimedia playback and scent recovery system and a multimedia and scent storage disc made in accordance with a third preferred embodiment of the present invention.

FIGS. 21–23 depict various front views of the multimedia playback and scent recovery system 700. Fabricated in a substantially vertical surface 713 of the multimedia playback and scent recovery system is an opening 714 for accepting a multimedia and scent storage disc 100. Also positioned in the substantially vertical surface 713 of the multimedia playback and scent recovery system 700 is an light-emitting diode 715 for indicating when the multimedia playback and scent recovery system is operating. In embodiments where the retractable semicircular shield 720 is opaque, the LED may be positioned somewhere else besides the substantially vertical surface so that it would be visible when the retractable shield is fully closed. Also visible in FIGS. 21–23 is the slot 721 in the housing 701 of the multimedia playback and scent recovery system 700 into which the shield 720 retracts.

Figure 24:
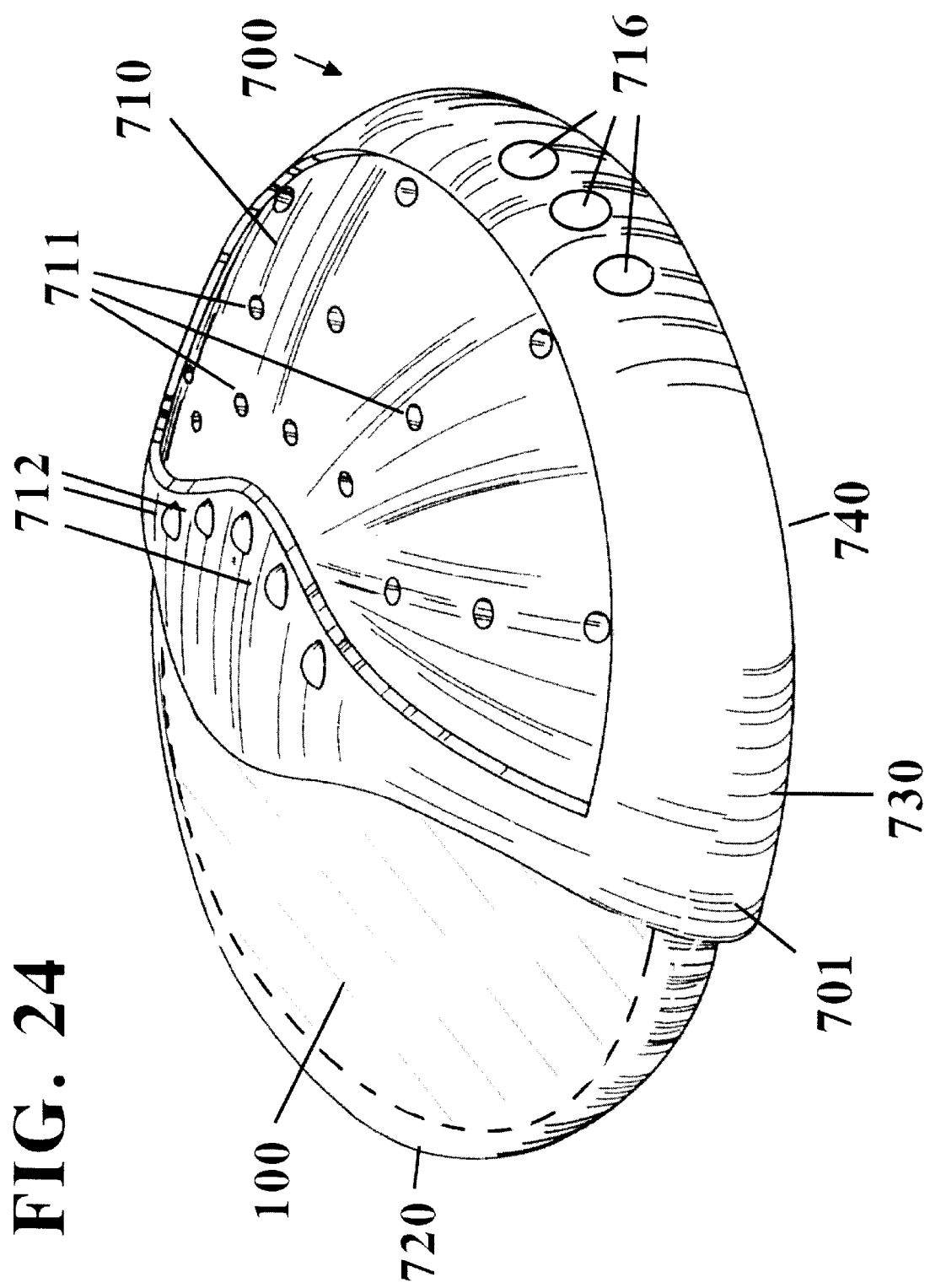
FIG. 24 depicts a side perspective view of a multimedia playback and scent recovery system and multimedia and scent storage disc made in accordance with a third preferred embodiment of the present invention.
Figure 25:
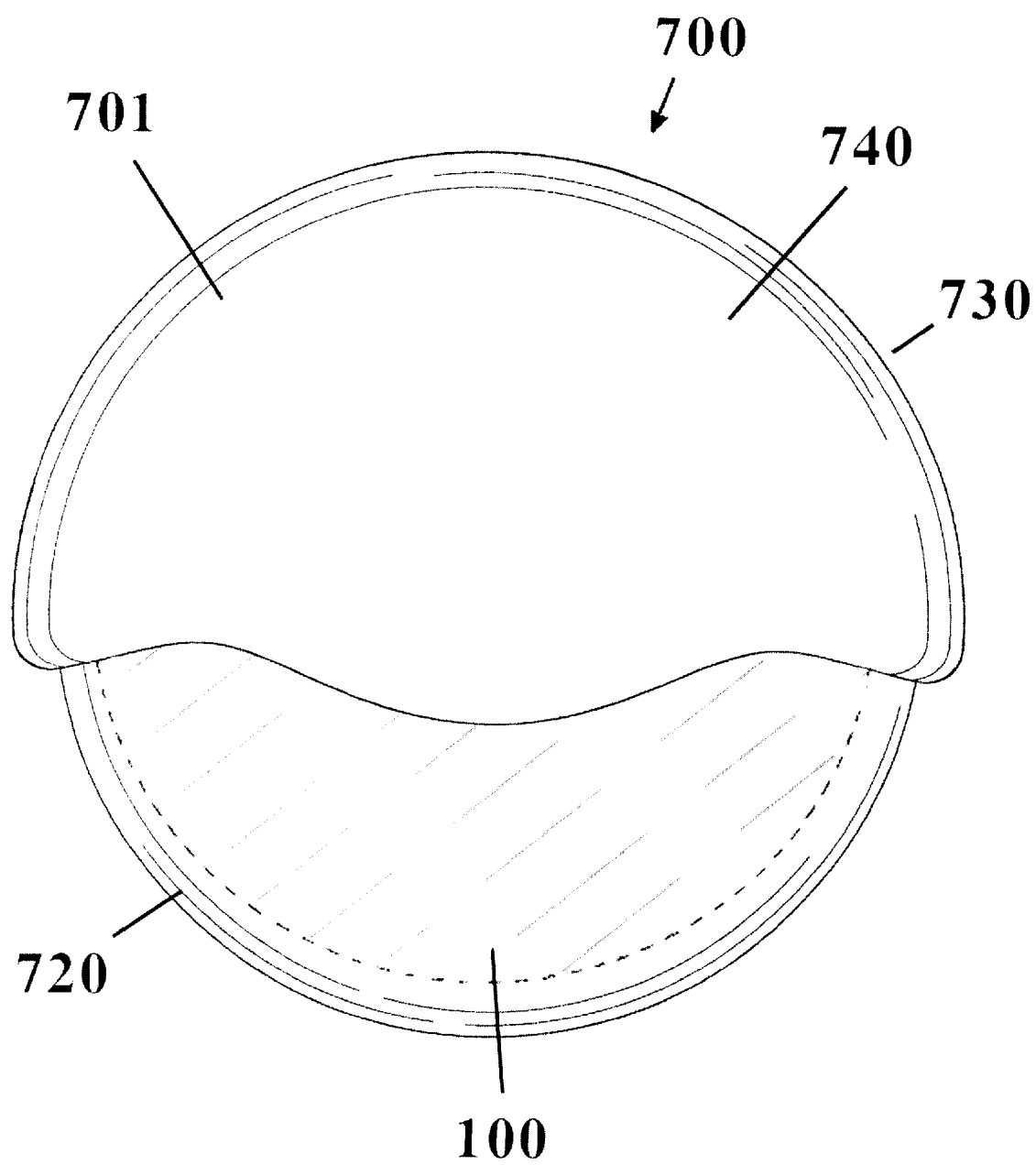
FIG. 25 depicts a bottom view of a multimedia playback and scent recovery system and multimedia and scent storage disc made in accordance with a third preferred embodiment of the present invention.

FIG. 24 shows a perspective side view of a multimedia playback and scent recovery system 700 made in accordance with the present invention. In this view interfacing means 716 is visible. Interfacing means 716 may comprise any number of electrical or optical connections known to those skilled in the art for connecting the multimedia playback and scent recovery system to peripheral components, for example, a computer game play station, or an audio-visual receiver and speaker system, or a computer. These peripherals interconnections will provide options to those using the multimedia playback and scent recovery system.

The foregoing description of the present invention has been presented for purposes of illustration and description. It is not intended to be exhaustive or to limit the invention to the precise form disclosed, and many modifications and variations are possible in light of the above disclosures.

What is claimed is:

1. An integrated system for playback of multimedia information and recovery of scents for use in combination with the multimedia information comprising:

a multimedia and scent-bearing medium comprising:
   multimedia storage means for storing multimedia information; and scent storage means for storing at least one scent;
a multimedia player and scent recovery system for use in conjunction with the multimedia and scent-bearing medium comprising:
   multimedia playback means for recovering the multimedia information stored in the multimedia storage means;
   scent recovery means for recovering the scents stored in the scent storage means;
   user input and control means for permitting the user of the integrated system to input commands for controlling the playback of multimedia information and recovery of scents stored in the multimedia and scent-bearing medium;
   a housing for enclosing the multimedia playback means and scent recovery means, the housing being semicircular in shape and having an upper surface, said housing having a slot for accepting the multimedia and scent-bearing medium, the multimedia and scent-bearing medium partially extending outward from the slot when placed within the housing for playback purposes, and wherein the housing further comprises at least a plurality of vents in the upper surface of the housing that permit scents recovered from the multimedia and scent-bearing medium by the scent recovery means to be exhausted to the atmosphere;
   a retractable shield for covering the portion of the multimedia and scent-bearing medium extending beyond the slot, wherein the retractable shield can be moved between at least a partially open position where the multimedia and scent-bearing medium may be placed within the slot in the housing and a closed position where the multimedia and scent-bearing medium is protected during operation; and
   a motor drive for moving the retractable shield.

2. The integrated system of claim 1 wherein the user input and control means are mounted in the upper surface of the housing.

3. The integrated system of claim 1 wherein the retractable shield is made from a transparent material.

4. The integrated system of claim 1 wherein the retractable shield is made from a translucent material.

5. The integrated system of claim 1 wherein the retractable shield is made from opaque material.

6. The integrated system of claim 1 wherein the multimedia player and scent recovery system further comprises:
   display means for displaying information concerning multimedia playback and scent recovery.

7. The integrated system of claim 6 wherein the display means comprises a liquid crystal display.

8. A multimedia player and scent recovery system for use with a multimedia and scent storage medium in disc format, the multimedia and scent storage medium storing multimedia information and at least one scent, the multimedia and scent recovery system comprising:
   multimedia playback means for recovering the multimedia information stored in the multimedia and scent storage medium;
   scent recovery means for recovering the scents stored in the multimedia and scent storage medium;
   user input and control means for permitting the user of the integrated system to input commands for controlling the playback of multimedia information and recovery of scents stored in the multimedia and scent-bearing medium;
   a housing for enclosing the multimedia playback means and scent recovery means, the housing being semicircular in shape and having an upper surface, said housing having a slot for accepting the multimedia and scent-bearing medium, the multimedia and scent-bearing medium partially extending outward from the slot when placed within the housing for playback purposes, and wherein the housing further comprises at least a plurality of vents in the upper surface of the housing that permit scents recovered from the multimedia and scent-bearing medium by the scent recovery means to be exhausted to the atmosphere;
   a retractable shield for covering the portion of the multimedia and scent-bearing medium extending beyond the slot, wherein the retractable shield can be moved between at least a partially open position where the multimedia and scent-bearing medium may be placed within the slot in the housing and a closed position where the multimedia and scent-bearing medium is protected during operation; and
   a motor drive for moving the retractable shield.

9. The multimedia player and scent recovery system of claim 8 wherein the user input and control means are mounted in the upper surface of the housing.

10. The multimedia player and scent recovery system of claim 8 wherein the retractable shield is made from transparent material.

11. The multimedia player and scent recovery system of claim 8 wherein the retractable shield is made from translucent material.

12. The multimedia player and scent recovery system of claim 8 wherein the retractable shield is made from opaque material.

13. The multimedia player and scent recovery system of claim 8 further comprising:
   display means for displaying information concerning multimedia playback and scent recovery.

14. The multimedia player and scent recovery system of claim 13 wherein the display means comprises a liquid crystal display.

15. A portable system for playback of multimedia information and recovery of scents for use in combination with the multimedia information, the portable system comprising:
   a multimedia and scent-bearing medium comprising:
      multimedia storage means for storing multimedia information; and scent storage means for storing at least one scent, and wherein the multimedia information further comprises at least preprogrammed scent recovery and multimedia playback sequence information for use in coordinating multimedia playback and scent recovery so that they occur in a repeatable manner;
   a multimedia player and scent recovery system for use in conjunction with the multimedia and scent-bearing medium, wherein the multimedia and scent bearing medium is separate and removable, the multimedia player and scent recovery system comprising:
      multimedia playback means for recovering and playing back the multimedia information stored in the multimedia storage means;
      scent recovery means for recovering and releasing the scents stored in the scent storage means;
      user input and control means for permitting the user of the portable system to input commands for controlling the playback of multimedia information and recovery of scents stored in the multimedia and scent-bearing medium;

scent recovery and multimedia playback sequence editing means both for editing the pre-programmed scent recovery and multimedia playback sequence to create a user-specified scent recovery and multimedia playback sequence, and for creating entirely new user-specified scent recovery and multimedia playback sequences; and a housing for enclosing the multimedia playback means and scent recovery means, the housing having an upper surface and a slot for accepting the removable multimedia and scent-bearing medium, and wherein the housing further comprises at least one vent that permits scents recovered from the multimedia and scent-bearing medium by the scent recovery means to be exhausted to the atmosphere.

16. The portable system of claim 15, wherein the portable system may be used in combination with separate multimedia playback systems, the portable system further comprising:

an output multimedia port for connecting the portable system to separate multimedia playback systems so that the multimedia information recovered from the multimedia and scent-bearing medium can be replayed by the separate multimedia playback systems.

17. The portable system of claim 15 wherein the user input and control means are mounted in the upper surface of the housing.

18. The portable system of claim 15 wherein the at least one vent is positioned on the upper surface of the housing.

19. The portable system of claim 15 wherein the multimedia playback means further comprises:

display means for displaying visual multimedia information recovered from the multimedia storage means.

20. The portable system of claim 19 wherein the display means further comprises a liquid crystal display.

21. The portable system of claim 15 wherein the multimedia playback means further comprises:

display means for displaying scent recovery and multimedia playback sequence information for use in editing the sequence information to create new scent recovery and multimedia playback sequences.

22. The portable system of claim 21 wherein the display means further comprises a liquid crystal display.

23. The portable system of claim 15 wherein the scent recovery means further comprises:

scent release means for releasing the at least one scent from the scent storage means so that it escapes from the scent storage means and enters the atmosphere adjacent to the multimedia and scent-bearing medium;

duct means for ducting the released scent to the at least one vent; and fan means for providing a positive pressure to assist in exhausting the released scent from the interior of the housing to the exterior of the housing through the at least one vent in the housing.

24. The portable system of claim 23 wherein a plurality of scents are stored in the multimedia and scent-bearing medium, and wherein the multimedia storage means further records scent identification information for identifying the scents stored in the multimedia and scent-bearing medium.

25. The portable system of claim 24 wherein the scent release means is moveable and can be positioned adjacent to the different scents stored in the multimedia and scent-bearing medium, the scent release means further comprising:

scent release control means for interpreting both the scent recovery and multimedia playback sequence information and scent identification information recovered from the multimedia storage means and for generating a control signal to move the scent release means during scent release operations to reproduce the scent recovery and multimedia playback sequence; and scent release motor means for receiving the control signal generated by the scent release control means and for moving the scent release means to the scents to be released from the multimedia and scent-bearing medium during a scent recovery and multimedia playback sequence.

26. The portable system of claim 25 wherein the plurality of scents are heat-releasable and wherein the scent release means further comprises an heating means for heating the plurality of scents during scent recovery operations.

27. The portable system of claim 26 wherein the heating means comprises a laser.

28. The portable system of claim 26 wherein the heating means comprises an infrared heating element.

29. The portable system of claim 23 wherein the at least one scent is heat-releasable and wherein the scent release means further comprises an heating means for heating the at least one scent during scent recovery operations.

30. The portable system of claim 29 wherein the heating means comprises a laser.

31. The portable system of claim 29 wherein the heating means comprises an infrared heating element.

32. A portable system for playback of multimedia information and recovery and release of scents for use in combination with the multimedia information comprising:

a multimedia and scent-bearing disc comprising:
  a substrate;
  a scent storage region positioned on the substrate for storing at least one scent;
  a multimedia storage region positioned on the substrate for storing optically-encoded multimedia information; scent recovery and multimedia playback sequence information; and scent identification information;

a multimedia player and scent recovery and release system for use with the multimedia and scent-bearing disc, wherein the multimedia and scent-bearing disc is separate and removable, the multimedia player and scent recovery system comprising:

multimedia playback means for recovering and playing back the information stored in the multimedia storage region;

scent recovery means for recovering and releasing the scents stored in the scent storage region;

user input and control means for permitting the user of the integrated system to input commands for controlling the playback of multimedia information and recovery of scents stored in the multimedia and scent-bearing disc;

scent recovery and multimedia playback sequence editing means both for editing the pre-programmed scent recovery and multimedia playback sequence to create a user-specified scent recovery and multimedia playback sequence, and for creating entirely new user-specified scent recovery and multimedia playback sequences; and a housing for enclosing the multimedia playback means and scent recovery means, the housing having an upper surface and a slot for accepting the removable multimedia and scent-bearing disc, and wherein the housing further comprises at least one vent that permits scents recovered from the multimedia and scent-bearing disc by the scent recovery means to be exhausted to the atmosphere.

33. The portable system of claim 32 further comprising:

an output multimedia port for connecting the portable system to separate multimedia playback systems so that the multimedia information recovered from the multimedia and scent-bearing disc can be replayed by the separate multimedia playback systems.

34. The portable system of claim 32 wherein the user input and control means are mounted in the upper surface of the housing.

35. The portable system of claim 32 wherein the multimedia playback means further comprises:

display means for displaying visual multimedia information recovered from the multimedia storage region.

36. The portable system of claim 35 wherein the display means further comprises a liquid crystal display.

37. The portable system of claim 32 wherein the multimedia playback means further comprises:

display means for displaying scent recovery and multimedia playback sequence information for use in editing the sequence information to create new scent recovery and multimedia playback sequences.

38. The portable system of claim 37 wherein the display means further comprises a liquid crystal display.

39. The portable system of claim 32 the scent recovery means further comprises:

scent release means for releasing the at least one scent from the scent storage region so that it escapes from the scent storage region and enters the atmosphere adjacent to the multimedia and scent-bearing disc;

duct means for ducting the released scent to the at least one vent; and fan means for providing a positive pressure to assist in exhausting the released scent from the interior of the housing to the exterior of the housing through the at least one vent in the housing.

40. The portable system of claim 39 wherein a plurality of scents are stored in the multimedia and scent-bearing disc, and wherein the scent identification information identifies each of the scents stored in the multimedia and scent-bearing disc.

41. The portable system of claim 40 wherein the scent release means is moveable and can be positioned adjacent to the different scents stored in the multimedia and scent-bearing disc, the scent release means further comprising:

scent release control means for interpreting both the scent recovery and multimedia playback sequence information and scent identification information recovered from the multimedia storage region and for generating a control signal to move the scent release means during scent release operations to reproduce the scent recovery and multimedia playback sequence; and scent release motor means for receiving the control signal generated by the scent release control means and for moving the scent release means to the scents to be released from the multimedia and scent-bearing disc during a scent recovery and multimedia playback sequence.

42. The portable system of claim 41 wherein the plurality of scents are heat-releasable and wherein the scent release means further comprises an heating means for heating the scents during scent recovery operations.

43. The portable system of claim 42 wherein the heating means comprises a laser.

44. The portable system of claim 42 wherein the heating means comprises an infrared heating element.

45. The portable system of claim 39 wherein the at least one scent is heat-releasable and wherein the scent release means further comprises an heating means for heating the at least one scent during scent recovery operations.

46. The portable system of claim 45 wherein the heating means comprises a laser.

47. The portable system of claim 45 wherein the heating means comprises an infrared heating element.

* * * * *